US012674187B2

(12) United States Patent
Juillard et al.

(10) Patent No.: US 12,674,187 B2
(45) Date of Patent: Jul. 7, 2026

(54) **GRAM-POSITIVE BACTERIA OF THE SPECIES *LACTOCOCCUS LACTIS* OR *STREPTOCOCCUS THERMOPHILUS* HAVING A VERY LOW SURFACE PROTEOLYSIS, PROCESSES FOR OBTAINING THEM AND USES THEREOF**

(71) Applicants: INSTITUT NATIONAL DE RECHERCHE POUR L'AGRICULTURE, L'ALIMENTATION ET L'ENVIRONNEMENT, Paris (FR); INSTITUT NATIONAL DES SCIENCES ET INDUSTRIES DU VIVANT ET DE L'ENVIRONNEMENT, Paris (FR)

(72) Inventors: Vincent Juillard, Neuilly sur Seine (FR); Rozenn Gardan, Jouy-en-Josas (FR); Mylène Boulay, Villers-le-Bâcle (FR); Véronique Monnet, Montigny-le-Bretonneux (FR)

(73) Assignees: Institut National Des Sciences Et Industries Du Vivant Et De L'Environnement, Paris (FR); Institut National De Recherche Pour L'Agriculture, L'Alimentation Et L'Environnement, Paris (FR)

( * ) Notice: Subject to any disclaimer, the term of this patent is extended or adjusted under 35 U.S.C. 154(b) by 852 days.

(21) Appl. No.: 17/908,372

(22) PCT Filed: Mar. 5, 2021

(86) PCT No.: PCT/EP2021/055561
§ 371 (c)(1),
(2) Date: Aug. 31, 2022

(87) PCT Pub. No.: WO2021/176039
PCT Pub. Date: Sep. 10, 2021

(65) Prior Publication Data
US 2023/0101904 A1 Mar. 30, 2023

(30) Foreign Application Priority Data
Mar. 6, 2020 (FR) ...................................... 2002268

(51) Int. Cl.
| | |
|---|---|
| *C12N 1/21* | (2006.01) |
| *C12N 9/52* | (2006.01) |
| *C12N 15/74* | (2006.01) |
| *C12P 21/02* | (2006.01) |

(52) U.S. Cl.
CPC ............ *C12P 21/02* (2013.01); *C12N 15/746* (2013.01)

(58) Field of Classification Search
None
See application file for complete search history.

(56) References Cited

PUBLICATIONS

Lecomte et al., "*Streptococcus thermophilus*, an emerging and promising tool for heterologous expression: Advantages and future trends," Food Microbiology 53:2-9, 2016 (Year: 2016).*
UniProt Database Accession No. Q5M2Z4, Feb. 2020, 2 pages (Year: 2020).*
Maehara et al., "Characterization of three putative Lon proteases of Thermus thermophilus HB27 and use of their defective mutants as hosts for production of heterologous proteins," Extremophiles 12:285-296, 2008 (Year: 2008).*
UniProt Database Accession No. Q5M228, Feb. 2020, 2 pages (Year: 2020).*
UniProt Database Accession No. B9UZ65, Dec. 2019, 3 pages (Year: 2019).*
Lecomte et al., "The naturally competent strain *Streptococcus thermophilus* LMD-9 as a new tool to anchor heterologous proteins on the cell surface," Microbial Cell Factories 13:82, 2014, 14 pages (Year: 2014).*
GenPept Database Accession No. ADQ63619, Jan. 2014, 2 pages (Year: 2014).*
International Search Report mailed Jun. 2, 2021, issued in corresponding International Patent Application No. PCT/EP2021/055561, filed Mar. 5, 2021, 7 pages.
International Written Opinion mailed Jun. 2, 2021 issued in corresponding International Patent Application No. PCT/EP2021/055561, filed Mar. 5, 2021, 7 pages.
Hafeez, Z. et al., "New Insights into the Proteolytic System of *Streptococcus thermophilus*: Use of Isracidin to Characterize Cell-Associated Extracellular Peptidase Activities," Journal of Agricultural and Food Chemistry, vol. 63, No. 34, Aug. 24, 2015, pp. 7522-7531.
Hafeez, Z. et al., "Hydrolysis of milk-derived bioactive peptides by cell-associated extracellular 71, No. 4, Jul. 1, 2006, pp. 394-406. of *Streptococcus themophilus*," Appl Microbiol Biotechnol., vol. 97 No. 22, Sep. 28, 2013, pp. 9787-9799.
Savijoki, K. et al., "Proteolytic systems of lactic acid bacteria," Appl Microbiol Biotechnol, vol. 71, No. 4, Jul. 1, 2006, pp. 394-406.

* cited by examiner

*Primary Examiner* — David Steadman
(74) *Attorney, Agent, or Firm* — Christensen O'Connor Johnson Kindness PLLC

(57) ABSTRACT

The present invention relates to a bacterium, in which the expression and/or the activity of surface proteases is/are inhibited, to its preparation process and to the uses of this bacterium.

9 Claims, 6 Drawing Sheets
Specification includes a Sequence Listing.

[Fig.1]

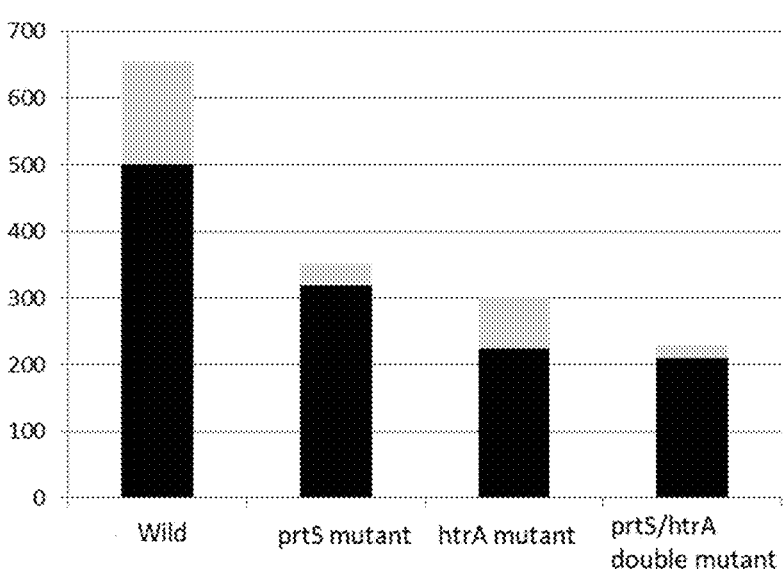

[Fig.2]

```
LMD9|STER_1612   MARKFESKALLENMERIKWKLLSIFTVLFLLFALFFELSNYTVELEGSAFDTKEVLTVBR
IL1403|ywdF      ~~MKRDKKINFKL~~~XDGISIGLIVVALLALFTP~TSYTVEMPGTTEPLGRMVEVEG
MG|llmg_2442     ~MNKRNKKISFKL~~~XGISIGLIIVALLVLVTP~TNYTVEMPGTTEPLGRMVEVEG
                  .*.* .  : :      .*  ;**    ;:.. *;.*;.* ;.***  ;   ; ::.*;

LMD9|STER_1612   RADSRSSINFVAVRQTRATLALXRLRAQFNDFAKLQTRREXRFGNYSDXDFMBINQFTRRT
IL1403|ywdF      SKDBMKDIPFLTTVQIARANLATRITSHPNSFTSIYSBQEMTGSLEDAQFNRVNQFTRRT
MG|llmg_2442     FKDEMKGDPFLTTVQIARANLATRITSHPNSFTSIYSBQEMTGSLEDAQFNRVNQFTRRT
                  * *; **.;  ;.;* ;.*.** *;*;;**.*;;.; ; ;* **; .* ;* *;*******

LMD9|STER_1612   SQNQAVYQGLTLAGSKEVSLBYSGVTYLQVADDGSFKGVLNISDTVTAVNGNTFDNGTDRI
IL1403|ywdF      AQNFTAIYQAFRLARKPYELKYEGVTYLDIAFNSTFKNKLELADTITAVNGQQFTSSACNI
MG|llmg_2442     AQNTAVYQAFRLARKPYELRYEGVTYLDIARNSTFKNKLELSDTITAVNGEEFRSSACNI
                  ;** *;.;.;.*  .;*;* ***;;.;;.  *;;;;**** ; * .;*;***

LMD9|STER_1612   KIYQGLKLGSRVKVTIMR~DGRRKTATSKIIKIANGNNGIGIGLTDHTKIRSPENVRFKI
IL1403|ywdF      AYVSRQKVGDSVTIEYTRIDGTRRSTGKYIKIANGRTGIGISLVDHTEVYTTPKVTVNA
MG|llmg_2442     AYVSRQKVGDSVTIEYTRIDGSRRSTGKYIKISNGRTGIGIGLYDHTEVYTDPKVTVNA
                  **;     *;*;;.*;; * * ;;;;.* *;*;****;*.****; ;   ;*;.;

LMD9|STER_1613   DGVGGFSAGIMFTLAIYDQVSGQDLKAGRRIAGTGTIEKDGAVGDIGGAYLSVKSAADSG
IL1403|ywdF      GSIGGFSAGRQMFTLEIYSQLTGKDLANGREIAGTGTIEHDGSIGQIGGVDKRVATASREG
MG|llmg_2442     GSIGGFSAGRQMFTLEIYSQLTGKNLRGGREIAGTGTIEHDGSIGQIGGVDKRVATASREG
                  ;.;******; ,*;;*;;*. *;;******;;;*;**.   ;*;;.*

LMD9|STER_1612   ADIFFYPBNLVTKDMKKADRCRNTBYQBAKEAABKLDTKMKIVFVKTAQEXISYLRKTK
IL1403|ywdF      AKVFLVPDSGTKKE~~~~~~~SSNBYLGAKTAABKLRTKMKIVPVKTIQDALDYLER~~
MG|llmg_2442     AKVFLVPDSGTKKE~~~~~~~SSNNYLGAKAAABKLRTRMKIVPVKTIQDALTYLER~~
                  *.;*;*;. ;. *      ;;.  ; **********  *;;*; **;*
```

[Fig.3]

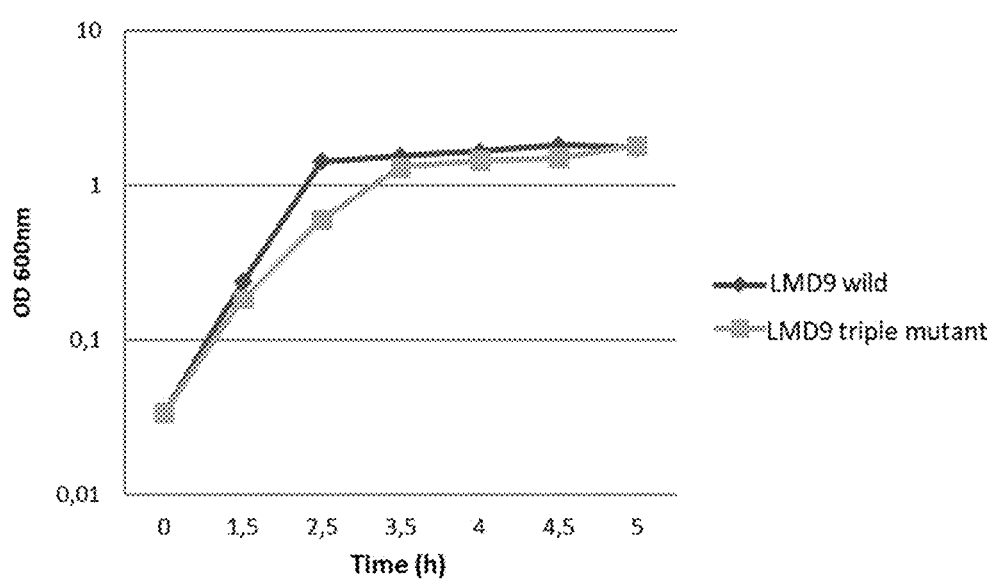

[Fig.4]

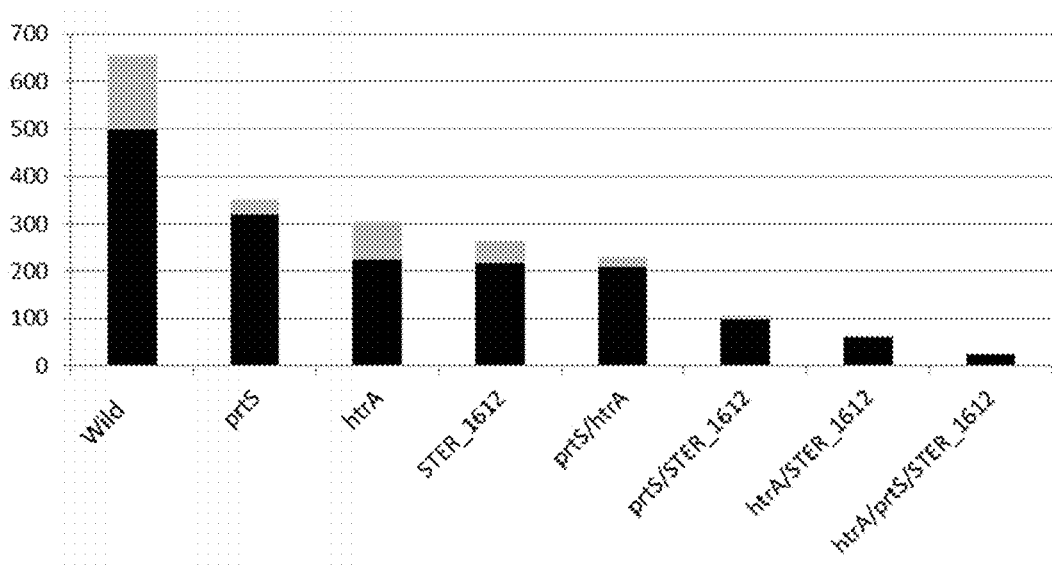

[Fig.5]

IL-10 :
MKKINLALLTLATLMGVSSTAVVFADDASQYSREDNNCTHFPVGQSHMLLELRTAFSQ
VKTFFQTKDQLDNILLTDSLMQDFKGYLGCQALSEMIQFYLVEVMPQAEKHGPEIKEH
LNSLGEKLKTLRMRLRRCHRFLPCENKSKAVEQVKSDFNKLQDQGVYKAMNEFDIFIN
CIEAYMMIKIKS
Elafine :
SAAVTGVPVKGQDTVKGRVPFNGQDPVKGQVSVKGQDKVKAQEPVKGPVSTKPGS
CPIILIRCAMLNPPNRCLKDTDCPGIKKCCEGSCGMACFVPQ

[Fig.6]
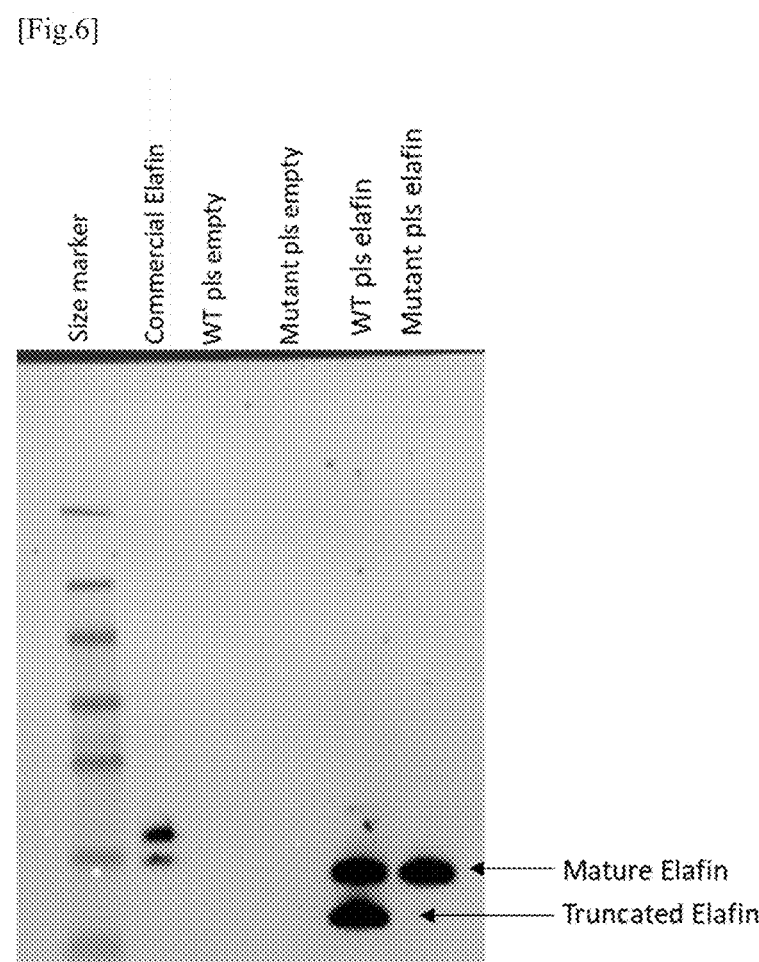
[Fig.7]
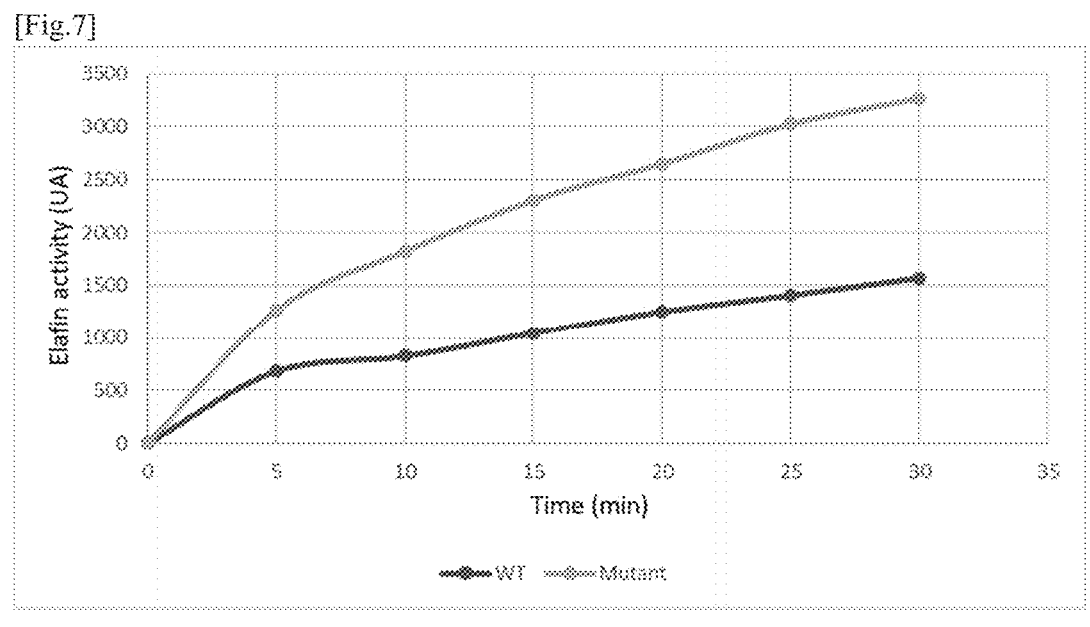

[Fig.8]
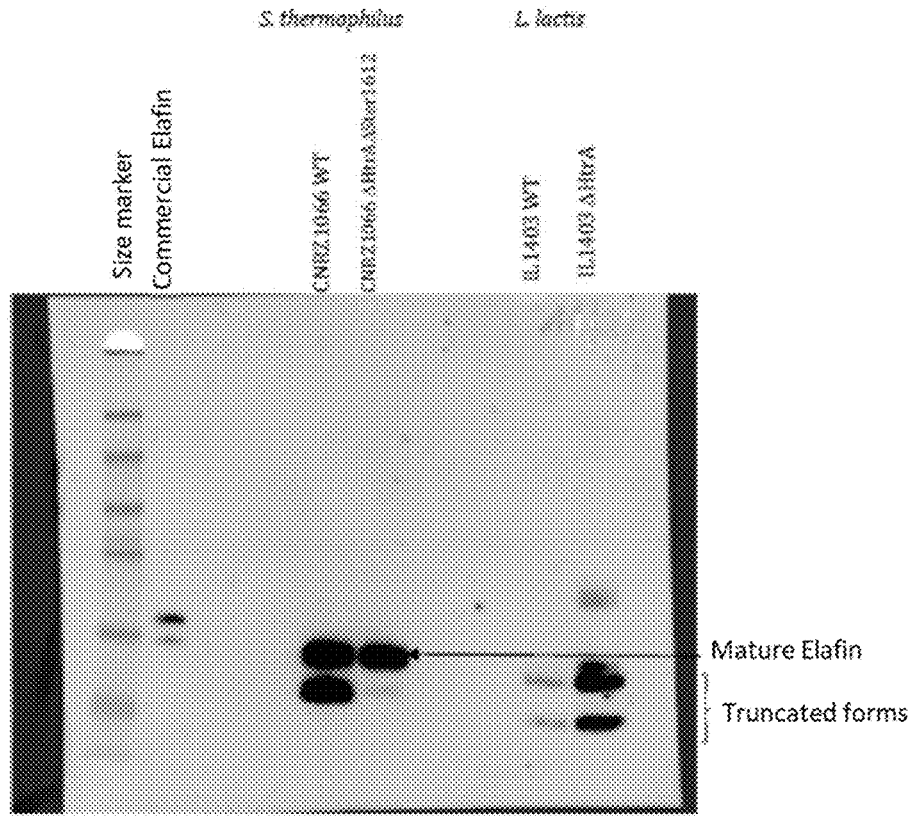
[Fig.9]
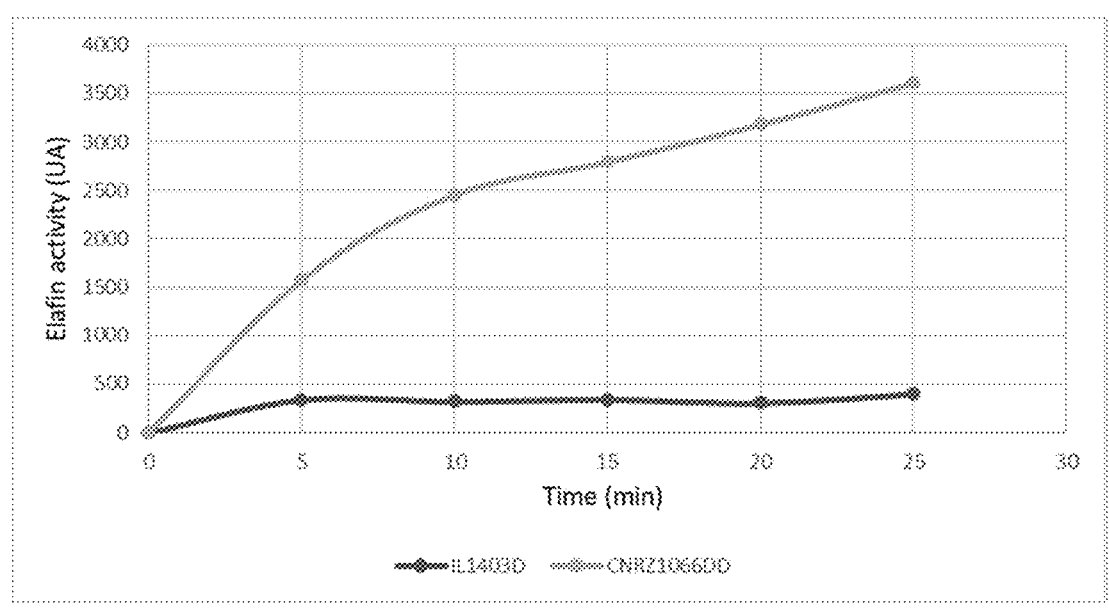

[Fig.10]
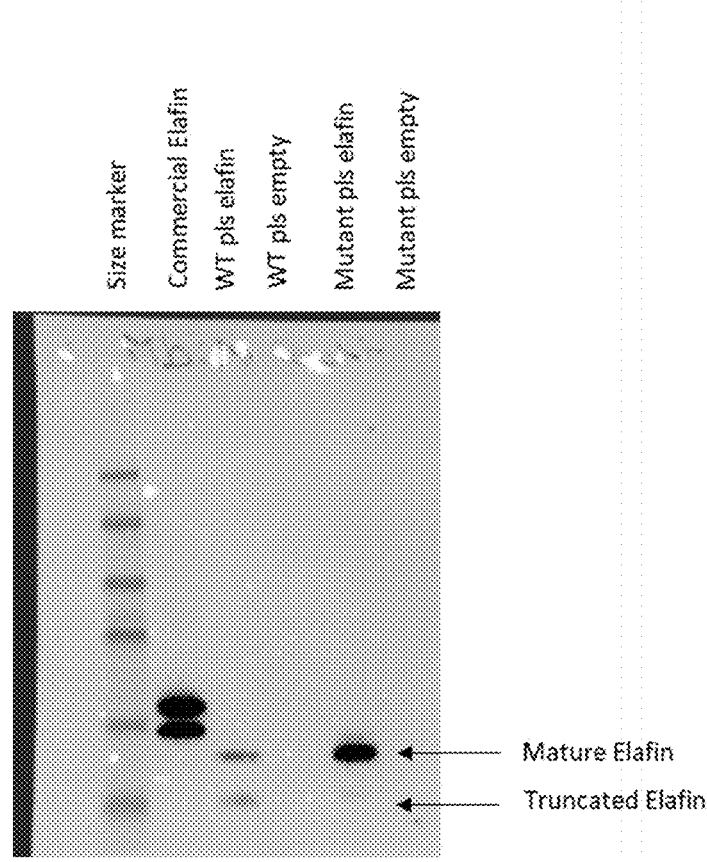

[Fig.11]
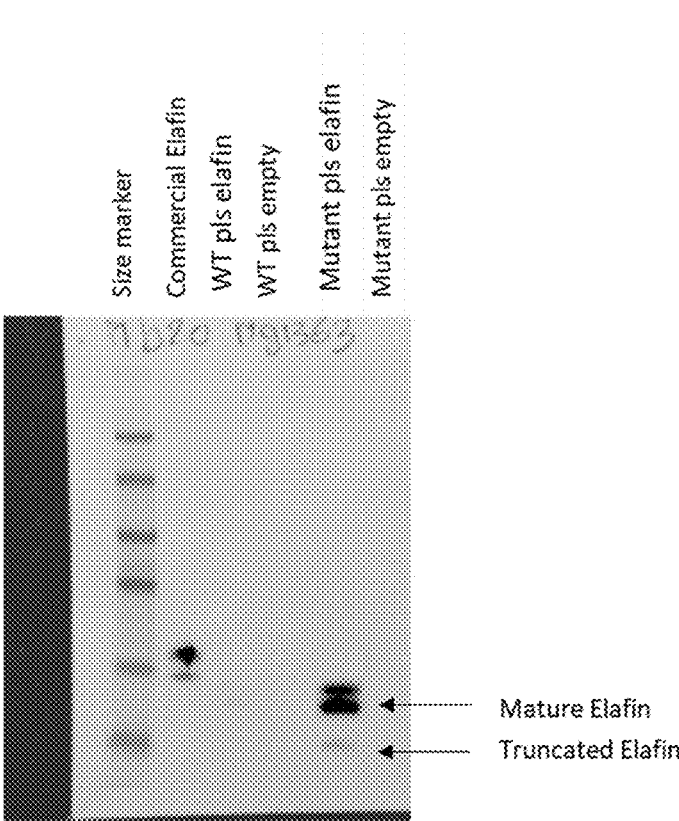

SEQUENCE LISTING

<160> NUMBER OF SEQ ID NOS: 43

<210> SEQ ID NO 1
<211> LENGTH: 22
<212> TYPE: PRT
<213> ORGANISM: Artificial Sequence
<220> FEATURE:
<223> OTHER INFORMATION: Consensus Sequence
<220> FEATURE:
<221> NAME/KEY: X
<222> LOCATION: (9)..(9)
<223> OTHER INFORMATION: X is H or K
<220> FEATURE:
<221> NAME/KEY: X
<222> LOCATION: (12)..(12)
<223> OTHER INFORMATION: X is S or A or T
<220> FEATURE:
<221> NAME/KEY: X
<222> LOCATION: (13)..(13)
<223> OTHER INFORMATION: X is I or L or V
<220> FEATURE:
<221> NAME/KEY: X
<222> LOCATION: (15)..(15)
<223> OTHER INFORMATION: X is D or Q
<220> FEATURE:
<221> NAME/KEY: X
<222> LOCATION: (19)..(19)
<223> OTHER INFORMATION: X is A or V
<220> FEATURE:

```
<221> NAME/KEY: X
<222> LOCATION: (20)..(20)
<223> OTHER INFORMATION: X is D or Y
<220> FEATURE:
<221> NAME/KEY: X
<222> LOCATION: (21)..(21)
<223> OTHER INFORMATION: X is K or L

<400> SEQUENCE: 1

Ile Ala Gly Thr Gly Thr Ile Glu Xaa Asp Gly Xaa Xaa Gly Xaa Ile
1               5                   10                  15

Gly Gly Xaa Xaa Xaa Lys
            20

<210> SEQ ID NO 2
<211> LENGTH: 358
<212> TYPE: PRT
<213> ORGANISM: Streptococcus thermophilus

<400> SEQUENCE: 2

Met Ala Asn Lys Thr Lys Ser Lys Ala Leu Leu Glu Lys Met Trp Arg
1               5                   10                  15

Ile Lys Trp Trp Leu Leu Ser Ile Phe Thr Val Leu Phe Leu Leu Phe
            20                  25                  30

Ala Leu Phe Phe Pro Leu Asn Asn Tyr Tyr Val Glu Leu Pro Gly Gly
        35                  40                  45

Ala Phe Asp Thr Lys Glu Val Leu Thr Val Asn Lys Lys Ala Asp Asp
    50                  55                  60

Ser Lys Gly Ser Tyr Asn Phe Val Ala Val Ala Gln Thr Lys Ala Thr
65                  70                  75                  80

Leu Ala Leu Met Leu Tyr Ala Gln Phe Asn Asp Phe Ala Lys Leu Gln
            85                  90                  95

Thr Ala Glu Glu Ala Thr Gly Asn Tyr Ser Asp Glu Asp Phe Met Arg
            100                 105                 110

Ile Asn Gln Phe Tyr Met Glu Thr Ser Gln Asn Gln Ala Val Tyr Gln
            115                 120                 125

Gly Leu Thr Leu Ala Gly Lys Glu Val Ser Leu Glu Tyr Met Gly Val
            130                 135                 140

Tyr Val Leu Gln Val Ala Asp Asp Ser Ser Phe Lys Gly Val Leu Asn
145                 150                 155                 160

Ile Ala Asp Thr Val Thr Ala Val Asn Gly Asn Thr Phe Asp Asn Ser
                165                 170                 175

Thr Asp Met Ile Lys Tyr Val Gln Gly Leu Lys Leu Gly Ser Lys Val
            180                 185                 190

Lys Val Thr Tyr Met Arg Asp Gly Lys Glu Lys Thr Ala Thr Gly Lys
            195                 200                 205

Ile Ile Lys Ile Ala Asn Gly Lys Asn Gly Ile Gly Ile Gly Leu Thr
    210                 215                 220

Asp His Thr Glu Ile Lys Ser Pro Glu Asn Val Lys Phe Lys Leu Asp
225                 230                 235                 240

Gly Val Gly Gly Pro Ser Ala Gly Leu Met Phe Thr Leu Ala Ile Tyr
                245                 250                 255

Asp Gln Val Ser Gly Gln Asp Leu Lys Ala Gly Arg Lys Ile Ala Gly
            260                 265                 270

Thr Gly Thr Ile Glu Lys Asp Gly Ala Val Gly Asp Ile Gly Gly Ala
            275                 280                 285

Tyr Leu Lys Val Lys Ser Ala Ala Asp Ser Gly Ala Asp Ile Phe Phe
```

```
          290                 295                 300

Val Pro Asn Asn Leu Val Thr Lys Glu Met Lys Lys Ala Asp Pro Asp
305                 310                 315                 320

Ala Lys Thr Asn Tyr Gln Glu Ala Lys Glu Ala Ala Glu Lys Leu Gly
                325                 330                 335

Thr Lys Met Lys Ile Val Pro Val Lys Thr Ala Gln Glu Ala Ile Asp
                340                 345                 350

Tyr Leu Lys Lys Thr Lys
          355

<210> SEQ ID NO 3
<211> LENGTH: 342
<212> TYPE: PRT
<213> ORGANISM: Lactococcus lactis

<400> SEQUENCE: 3

Met Lys Lys Asn Lys Lys Ile Asn Pro Lys Leu Lys Trp Gly Ile Ser
1               5                   10                  15

Ile Gly Leu Ile Val Val Ala Leu Leu Ala Leu Phe Tyr Pro Thr Ser
                20                  25                  30

Tyr Tyr Val Glu Met Pro Gly Thr Thr Glu Pro Leu Gly Lys Met Val
            35                  40                  45

Lys Val Glu Gly Lys Lys Asp Glu His Lys Gly Asp Phe Phe Leu Thr
        50                  55                  60

Thr Val Gln Ile Ala Arg Ala Asn Leu Ala Thr Met Ile Tyr Ser His
65                  70                  75                  80

Phe Asn Ser Phe Thr Ser Ile Tyr Ser Glu Gln Glu Met Thr Gly Gly
                85                  90                  95

Leu Asn Asp Ala Gln Phe Asn Arg Val Asn Gln Phe Tyr Met Glu Thr
                100                 105                 110

Ala Gln Asn Thr Ala Ile Tyr Gln Ala Phe Lys Leu Ala Asn Lys Pro
            115                 120                 125

Tyr Glu Leu Lys Tyr Glu Gly Val Tyr Val Leu Asp Ile Ala Lys Asn
        130                 135                 140

Ser Thr Phe Lys Asn Lys Leu Glu Leu Ala Asp Thr Ile Thr Ala Val
145                 150                 155                 160

Asn Gly Gln Gln Phe Thr Ser Ser Ala Asp Met Ile Ala Tyr Val Ser
                165                 170                 175

Lys Gln Lys Val Gly Asp Ser Val Thr Ile Glu Tyr Thr Arg Ile Asp
            180                 185                 190

Gly Thr Lys His Lys Ser Thr Gly Lys Tyr Ile Lys Ile Ala Asn Gly
            195                 200                 205

Lys Thr Gly Ile Gly Ile Ser Leu Val Asp His Thr Glu Val Val Thr
        210                 215                 220

Thr Pro Lys Val Thr Val Asn Ala Gly Ser Ile Gly Gly Pro Ser Ala
225                 230                 235                 240

Gly Met Met Phe Thr Leu Glu Ile Tyr Ser Gln Leu Thr Gly Lys Asp
                245                 250                 255

Leu Arg Asn Gly Arg Glu Ile Ala Gly Thr Gly Thr Ile Glu His Asp
            260                 265                 270

Gly Ser Ile Gly Gln Ile Gly Gly Val Asp Lys Lys Val Ala Thr Ala
        275                 280                 285

Ser Lys Glu Gly Ala Lys Val Phe Leu Val Pro Asp Ser Gly Thr Lys
        290                 295                 300
```

-continued

```
Lys Glu Ser Ser Asn Asn Tyr Leu Gly Ala Lys Thr Ala Ala Lys Lys
305             310             315             320

Leu Lys Thr Lys Met Lys Ile Val Pro Val Lys Thr Ile Gln Asp Ala
            325             330             335

Leu Asp Tyr Leu Glu Lys
        340

<210> SEQ ID NO 4
<211> LENGTH: 343
<212> TYPE: PRT
<213> ORGANISM: Lactococcus lactis

<400> SEQUENCE: 4

Met Asn Lys Lys Asn Lys Lys Ile Ser Pro Lys Leu Lys Trp Gly Ile
1               5               10              15

Ser Ile Gly Leu Ile Ile Val Ala Leu Leu Val Leu Val Tyr Pro Thr
            20              25              30

Asn Tyr Tyr Val Glu Met Pro Gly Thr Thr Glu Pro Leu Gly Lys Met
        35              40              45

Val Lys Val Glu Gly Lys Lys Asp Glu His Lys Gly Asp Phe Phe Leu
    50              55              60

Thr Thr Val Gln Ile Ala Arg Ala Asn Leu Ala Thr Met Ile Tyr Ser
65              70              75              80

His Phe Asn Ser Phe Thr Ser Ile Tyr Ser Glu Gln Glu Met Thr Gly
            85              90              95

Gly Leu Asn Asp Ala Gln Phe Asn Arg Val Asn Gln Phe Tyr Met Glu
        100             105             110

Thr Ala Gln Asn Thr Ala Val Tyr Gln Ala Phe Lys Leu Ala Asn Lys
        115             120             125

Pro Tyr Glu Leu Lys Tyr Glu Gly Val Tyr Val Leu Asp Ile Ala Lys
        130             135             140

Asn Ser Thr Phe Lys Asn Lys Leu Glu Leu Ser Asp Thr Ile Thr Ala
145             150             155             160

Val Asn Gly Glu Glu Phe Lys Ser Ser Ala Asp Met Ile Ala Tyr Val
            165             170             175

Ser Lys Gln Lys Val Gly Asp Ser Val Thr Ile Glu Tyr Thr Arg Ile
            180             185             190

Asp Gly Ser Lys His Lys Ser Thr Gly Lys Tyr Ile Lys Ile Ser Asn
        195             200             205

Gly Lys Thr Gly Ile Gly Ile Gly Leu Val Asp His Thr Glu Val Val
        210             215             220

Thr Asp Pro Lys Val Thr Val Asn Ala Gly Ser Ile Gly Gly Pro Ser
225             230             235             240

Ala Gly Met Met Phe Thr Leu Glu Ile Tyr Ser Gln Leu Thr Gly Lys
            245             250             255

Asn Leu Arg Gly Gly Arg Glu Ile Ala Gly Thr Gly Thr Ile Glu His
        260             265             270

Asp Gly Ser Ile Gly Gln Ile Gly Gly Val Asp Lys Lys Val Ala Thr
        275             280             285

Ala Ser Lys Glu Gly Ala Lys Val Phe Leu Val Pro Asp Ser Gly Thr
    290             295             300

Lys Lys Glu Ser Ser Asn Asn Tyr Leu Gly Ala Lys Ala Ala Ala Lys
305             310             315             320

Lys Leu Lys Thr Lys Met Lys Ile Val Pro Val Lys Thr Ile Gln Asp
            325             330             335
```

```
Ala Leu Thr Tyr Leu Glu Lys
            340

<210> SEQ ID NO 5
<211> LENGTH: 1077
<212> TYPE: DNA
<213> ORGANISM: Streptococcus thermophilus

<400> SEQUENCE: 5
gtggcaaaca agacaaaatc taaagcgcta ttagagaaaa tgtggcgtat taagtggtgg      60
ttattaagta tttttacggt acttttcctc ctttttgccc tctttttccc gctcaataat     120
tactatgtgg agcttccggg tggtgctttt gataccaagg aagtcttgac agtgaataag     180
aaagctgatg attctaaggg ctcctataat tttgtggcgg tggctcaaac caaggcgact     240
ttggccttga tgctctatgc tcagtttaat gattttgcaa agcttcaaac ggctgaagag     300
gcaactggaa attactctga tgaagatttc atgcgcatca accaatttta catggagact     360
tctcaaaacc aagcggttta tcaggccttg actctggctg gtaaggaggt tagtttggag     420
tatatgggtg tctatgtgct tcaggttgct gatgattcta gcttcaaggg tgtcctcaat     480
attgctgata cggtgacggc tgttaatggt aatacctttg ataattctac tgacatgatt     540
aaatacgttc aaggacttaa gctgggttca aaggtcaagg tcacttatat gagagatggc     600
aaagaaaaga ctgctactgg taagattatt aagattgcca atggcaaaaa tggtattggt     660
atcggcctaa cggaccatac tgagatcaag agtcctgaga atgttaagtt taaactggat     720
ggtgtcggtg ggccaagtgc tggtcttatg tttaccttgg ctatttacga tcaggtgtct     780
ggtcaagacc tcaaggctgg ccgcaagatt gctggtacag gaactattga aaaagatggg     840
gctgtcggtg atatcggtgg ggcctatctc aaggtgaaat ctgcggctga tagtggcgca     900
gacattttct tcgtgccaaa taatctagta actaaggaaa tgaaaaaggc tgatccggat     960
gccaagacta attatcaaga ggccaaggaa gctgccgaga aactggggac caagatgaaa    1020
atcgtccctg ttaaaacagc tcaagaagcc attgattatt tgaaaaagac taaatga      1077

<210> SEQ ID NO 6
<211> LENGTH: 1029
<212> TYPE: DNA
<213> ORGANISM: Lactococcus lactis

<400> SEQUENCE: 6
atgaaaaaaa ataaaaaaat taatcccaaa ttaaaatggg gaatctcgat tggtctaatt      60
gttgttgccc ttttagcttt attttatcca acgagttact atgtggaaat gcccggaaca     120
accgagcctt tagggaaaat ggtcaaagtt gaaggcaaaa aagatgaaca taaaggtgat     180
tttttcctga cgactgtcca aattgcacga gcaaatcttg ctacaatgat ttacagccat     240
tttaatagtt ttacaagcat ttacagtgag caagaaatga ctggtggact taacgacgca     300
cagttcaacc gtgtcaacca gttttacatg gaaacggcac agaatacagc gatttatcaa     360
gcttttaaat tagctaataa accttatgaa cttaaatatg aaggcgttta tgtccttgat     420
attgccaaaa attcgacctt taaaaataag ctagaacttg cagatacgat tacagcagtc     480
aatggtcaac agtttacatc aagtgccgac atgattgctt atgtttccaa acaaaaagtc     540
ggtgattcag taacgattga atacacgaga attgacggca caaagcacaa gtcaactggc     600
aaatacatca aaattgctaa tggaaaaaca ggaattggga tcagcctagt tgaccatact     660
gaagtcgtga cgactccaaa agttactgtc aacgcgggtt caatcggtgg tccctctgcg     720
```

-continued

```
gggatgatgt ttacactaga aatttacagt cagttgacag gaaaagattt gcgaaacggt    780
cgcgaaattg ctggaactgg aacgattgaa catgacggaa gcattggcca aatcggcggt    840
gttgataaaa aagtagccac agcgagcaaa gaaggggcaa aggtcttctt agtgcctgac    900
tcaggcacca aaaaggaaag cagcaacaat taccttggag ccaaaaccgc agctaaaaaa    960
ctaaaaacga agatgaaaat cgttcccgtc aaaactattc aggacgcttt agattattta   1020
gaaaaataa                                                            1029
```

```
<210> SEQ ID NO 7
<211> LENGTH: 1032
<212> TYPE: DNA
<213> ORGANISM: Lactococcus lactis

<400> SEQUENCE: 7
ttatttttct aaataagtta aagcgtcctg aatagtcttg acgggaacaa ttttcatctt     60 cgttttaat tttttagcgg ctgctttggc tccaagatag ttattgctgc tttctttttt    120
ggtgcctgag tcaggaacta agaaaacttt tgcgccttct ttgctagcag tagctacttt    180
tttatcaacc ccaccgattt ggccaatgct tccatcatgt tcaatcgttc cagttcctgc    240
tatttcgcga ccaccacgta aatttttacc tgtcaactga ctgtaaatct ctagtgtaaa    300
catcattccg gcagatggtc caccgattga acctgcattg actgtaactt ttgggtctgt    360
gactacttca gtatggtcaa ctagtccaat tccgattccg gtttttccat tagagatttt    420
gatatatttt ccagtagact tgtgtttact gccatcaatc cgtgtatatt caatggtaac    480
tgaatcgccg acttttttgct tcgaaacgta agcaatcata tctgcacttg atttaaattc    540
ttccccattg actgctgtaa tcgtgtccga aagttccaat ttatttttaa aagtcgaatt    600
tttagcgata tcaaggacat aaacccccttc atatttcagt tcatagggtt tatttgccaa    660
cttgaaggcc tgataaacgg ctgtattttg tgcagtttcc atgtaaaact ggttgacacg    720
attgaactgc gcatcattaa gaccaccggt catttcttgt tcactgtaaa tgcttgtaaa    780
actattaaaa tgactgtaaa tcattgtggc aagattagca cgcgcaattt gaacggtagt    840
aaggaaaaag tcacctttgt gctcatcttt ttttccttca actttgacca tttttccctaa    900 tggctcggtt gttccaggca tttccacata gtaatttgtt ggatacacta aaacaaggag    960
agcgacaata atcaggccaa tagagatgcc ccatttttaat ttgggactga tttttttatt   1020
ttttttgttc at                                                        1032
```

```
<210> SEQ ID NO 8
<211> LENGTH: 411
<212> TYPE: PRT
<213> ORGANISM: Streptococcus thermophilus

<400> SEQUENCE: 8

Met Lys Lys Ile Asn Trp Lys Lys Ile Val Ala Pro Ile Ala Met Leu
1               5                   10                  15

Ile Ile Gly Leu Leu Gly Gly Leu Leu Gly Ala Phe Ile Leu Leu Thr
                20                  25                  30

Ala Ala Gly Val Ser Phe Thr Asn Thr Thr Asp Thr Gly Ala Lys Thr
            35                  40                  45

Ala Lys Thr Val Tyr Thr Asn Ile Thr Asp Thr Thr Lys Ala Val Lys
        50                  55                  60

Lys Val Gln Asn Ala Val Val Ser Val Ile Asn Tyr Gln Glu Gly Ser
65                  70                  75                  80
```

-continued

```
Ser Ser Asp Ser Leu Asn Asp Leu Tyr Gly Arg Ile Phe Gly Gly Gly
            85              90              95

Asp Ser Ser Asp Ser Ser Gln Glu Asn Ser Lys Asp Ser Asp Gly Leu
            100             105             110

Gln Val Ala Gly Glu Gly Ser Gly Val Ile Tyr Lys Lys Asp Gly Lys
            115             120             125

Glu Ala Tyr Ile Val Thr Asn Asn His Val Val Asp Gly Ala Lys Lys
        130             135             140

Leu Glu Ile Met Leu Ser Asp Gly Ser Lys Ile Thr Gly Glu Leu Val
145             150             155             160

Gly Lys Asp Thr Tyr Ser Asp Leu Ala Val Val Lys Val Ser Ser Asp
            165             170             175

Lys Ile Thr Thr Val Ala Glu Phe Ala Asp Ser Asn Ser Leu Thr Val
            180             185             190

Gly Glu Lys Ala Ile Ala Ile Gly Ser Pro Leu Gly Thr Glu Tyr Ala
            195             200             205

Asn Ser Val Thr Glu Gly Ile Val Ser Ser Leu Ser Arg Thr Ile Thr
        210             215             220

Met Gln Asn Asp Asn Gly Glu Thr Val Ser Thr Asn Ala Ile Gln Thr
225             230             235             240

Asp Ala Ala Ile Asn Pro Gly Asn Ser Gly Gly Ala Leu Val Asn Ile
            245             250             255

Glu Gly Gln Val Ile Gly Ile Asn Ser Ser Lys Ile Ser Ser Thr Ser
            260             265             270

Ala Val Ala Gly Ser Ala Val Glu Gly Met Gly Phe Ala Ile Pro Ser
            275             280             285

Asn Asp Val Val Glu Ile Ile Asn Gln Leu Glu Lys Asp Gly Lys Val
        290             295             300

Thr Arg Pro Ala Leu Gly Ile Ser Ile Ala Asp Leu Asn Ser Leu Ser
305             310             315             320

Ser Ser Ala Thr Ser Lys Leu Asp Leu Pro Asp Glu Val Lys Ser Gly
            325             330             335

Val Val Val Gly Ser Val Gln Lys Gly Met Pro Ala Asp Gly Lys Leu
            340             345             350

Gln Glu Tyr Asp Val Ile Thr Glu Ile Asp Gly Lys Lys Ile Ser Ser
            355             360             365

Lys Thr Asp Ile Gln Thr Asn Leu Tyr Ser His Ser Ile Gly Asp Thr
        370             375             380

Ile Lys Val Thr Phe Tyr Arg Gly Lys Asp Lys Lys Thr Val Asp Leu
385             390             395             400

Lys Leu Thr Lys Ser Thr Glu Asp Ile Ser Asp
            405             410
```

<210> SEQ ID NO 9
<211> LENGTH: 1618
<212> TYPE: PRT
<213> ORGANISM: Streptococcus thermophilus

<400> SEQUENCE: 9

```
Met Lys Lys Lys Glu Thr Phe Ser Leu Arg Lys Tyr Lys Ile Gly Thr
1               5               10              15

Val Ser Val Leu Leu Gly Ala Val Phe Leu Phe Ala Gly Ala Pro Ser
            20              25              30

Val Ala Ala Asp Glu Leu Thr Ser Leu Val Glu Thr Lys Val Glu Ala
```

-continued

```
              35                    40                    45
Thr Val Pro Asp Ala Ile Val Ser Glu Ser Ala Ser Glu Ser Pro Val
     50                    55                    60

Ala Glu Glu Leu Val Asp Thr Ser Val Glu Ala Thr Ser Thr Asp Val
65                    70                    75                    80

Thr Thr Thr Asp Asn Glu Glu Glu Thr Leu Gly Ser Glu Ser Pro Val
                    85                    90                    95

Val Glu Glu Leu Val Asp Thr Ser Val Glu Ala Thr Pro Thr Asp Val
                    100                   105                   110

Thr Thr Thr Asp Asn Val Glu Glu Thr Leu Gly Ser Glu Ala Leu Glu
                    115                   120                   125

Asn Ile Thr Asn Thr Glu Val Glu Ala Thr Gln Pro Ala Val Glu Thr
     130                   135                   140

Pro Ala Ile Ser Glu Lys Lys Val Glu Glu Glu Lys Leu Ser Val
145                   150                   155                   160

Ala Asp Glu Thr Thr Ala Ile Thr Asn Gln Glu Glu Ala Lys Pro Gln
                    165                   170                   175

Asn Ile Asp Ser Asn Thr Ile Ile Thr Val Pro Lys Val Trp Asp Ser
                    180                   185                   190

Gly Tyr Lys Gly Glu Gly Thr Val Val Ala Ile Ile Asp Ser Gly Leu
                    195                   200                   205

Asp Val Asp His Asp Val Leu His Ile Ser Asp Leu Ser Thr Ala Lys
     210                   215                   220

Tyr Lys Ser Glu Lys Glu Ile Glu Ala Ala Lys Glu Val Ala Gly Ile
225                   230                   235                   240

Ser Tyr Gly Glu Trp Phe Asn Asp Lys Val Val Phe Gly Tyr Asn Tyr
                    245                   250                   255

Val Asp Val Asn Thr Val Leu Lys Glu Glu Asp Lys Arg Ser His Gly
                    260                   265                   270

Met His Val Thr Ser Ile Ala Thr Gly Asn Pro Thr Gln Pro Val Ala
                    275                   280                   285

Gly Gln Leu Met Tyr Gly Val Ala Pro Glu Ala Gln Val Met Phe Met
     290                   295                   300

Arg Val Phe Ser Asp Leu Lys Ala Thr Thr Gly Ala Ala Leu Tyr Val
305                   310                   315                   320

Lys Ala Ile Glu Asp Ala Val Lys Leu Gly Ala Asp Ser Ile Asn Leu
                    325                   330                   335

Ser Leu Gly Gly Ala Asn Gly Ser Val Val Asn Met Asn Glu Asn Val
                    340                   345                   350

Thr Ala Ala Ile Glu Ala Ala Arg Arg Ala Gly Val Ser Val Val Ile
                    355                   360                   365

Ala Ala Gly Asn Asp Gly Thr Phe Gly Ser Gly His Ser Asn Pro Ser
     370                   375                   380

Ala Asp Tyr Pro Asp Tyr Gly Leu Val Gly Ala Pro Ser Thr Ala Arg
385                   390                   395                   400

Asp Ala Ile Ser Val Ala Ser Tyr Asn Asn Thr Thr Val Gly Ser Lys
                    405                   410                   415

Val Ile Asn Ile Ile Gly Leu Glu Asn Asn Ala Asp Leu Asn Tyr Gly
                    420                   425                   430

Lys Ser Ser Phe Asp Asn Pro Glu Lys Ser Pro Val Pro Phe Glu Ile
                    435                   440                   445

Gly Lys Glu Tyr Glu Tyr Val Tyr Ala Gly Ile Gly Gln Ala Ser Asp
     450                   455                   460
```

```
Phe Asp Gly Leu Asp Leu Thr Gly Lys Leu Ala Leu Ile Lys Arg Gly
465                 470                 475                 480

Thr Ile Ser Phe Ser Glu Lys Ile Ala Asn Ala Thr Ala Ala Gly Ala
                485                 490                 495

Val Gly Val Val Ile Phe Asn Ser Arg Pro Asp Glu Ala Asn Val Ser
                500                 505                 510

Met Gln Leu Asp Asp Thr Ala Ile Ala Ile Pro Ser Val Phe Ile Pro
            515                 520                 525

Leu Glu Phe Gly Glu Ala Leu Ala Ala Asn Ser Tyr Lys Ile Ala Phe
            530                 535                 540

Asn Asn Glu Thr Asp Ile Arg Pro Asn Pro Glu Ala Gly Leu Leu Ser
545                 550                 555                 560

Asp Phe Ser Ser Trp Gly Leu Ser Ala Asp Gly Glu Leu Lys Pro Asp
                565                 570                 575

Leu Ala Ala Pro Gly Gly Ala Ile Tyr Ala Ala Ile Asn Asp Asn Asp
                580                 585                 590

Tyr Ala Asn Met Gln Gly Thr Ser Met Ala Ser Pro His Val Ala Gly
            595                 600                 605

Ala Ala Val Leu Val Lys Gln Tyr Leu Gln Ala Thr Tyr Pro Thr Lys
            610                 615                 620

Ser Pro Gln Glu Ile Glu Ala Leu Val Lys His Leu Leu Met Ser Thr
625                 630                 635                 640

Ala Lys Ala His Val Asn Lys Glu Thr Thr Ala Tyr Thr Ser Pro Arg
                645                 650                 655

Gln Gln Gly Ala Gly Ile Ile Asp Thr Ala Ala Ala Ile Ser Thr Gly
                660                 665                 670

Leu Tyr Leu Thr Gly Glu Asp Gly Tyr Gly Ser Ile Thr Leu Gly Asn
            675                 680                 685

Val Glu Asp Thr Phe Ser Phe Thr Val Thr Leu His Asn Ile Thr Asn
            690                 695                 700

Glu Asp Lys Thr Leu Asn Tyr Ser Thr Gln Leu Thr Thr Asp Thr Val
705                 710                 715                 720

Gln Asn Gly Leu Ile Thr Leu Ala Pro Arg Leu Leu Ala Glu Ile Pro
                725                 730                 735

Gly Gly Lys Val Thr Val Gln Ala Asn Ser Ser Thr Thr Val Thr Ile
                740                 745                 750

Asn Val Asp Ala Ser Ser Phe Ala Glu Glu Leu Thr Gly Leu Met Lys
            755                 760                 765

Asn Gly Tyr Tyr Leu Glu Gly Phe Val Arg Phe Thr Asp Val Ala Asp
            770                 775                 780

Gly Gly Asp Ile Val Ser Ile Pro Tyr Ile Gly Phe Arg Gly Glu Phe
785                 790                 795                 800

Gln Asn Leu Ala Val Leu Glu Glu Pro Ile Tyr Asn Leu Ile Ala Asp
                805                 810                 815

Gly Lys Gly Gly Phe Tyr Phe Glu Pro Val Thr Ala Gln Pro Asp Ser
                820                 825                 830

Val Asp Ile Ser His His Tyr Thr Gly Leu Val Thr Gly Ser Thr Glu
            835                 840                 845

Leu Ile Tyr Ser Thr Asp Lys Arg Ser Asp Phe Ala Ile Lys Lys Thr
            850                 855                 860

Leu Gly Thr Phe Lys Asn Glu Ala Gly Tyr Phe Val Leu Glu Leu Asp
865                 870                 875                 880
```

-continued

```
Glu Ser Gly Lys Pro His Leu Ala Ile Ser Pro Asn Gly Asp Asp Asn
              885                 890                 895

Gln Asp Ser Leu Ala Phe Lys Gly Val Phe Leu Arg Asn Tyr Thr Asp
              900                 905                 910

Leu Val Ala Ser Val Tyr Ala Ala Asp Asp Thr Glu Arg Thr Asn Pro
              915                 920                 925

Leu Trp Glu Ser Gln Pro Gln Ser Gly Asn Lys Asn Phe Tyr Ser Gly
         930                 935                 940

Asp Pro Lys Asn Pro Lys Ser Ser Ile Ile Tyr Pro Thr Glu Trp Asn
945                 950                 955                 960

Gly Thr Asp Ser Glu Gly Asn Ala Leu Ala Asp Gly Lys Tyr Gln Tyr
              965                 970                 975

Val Leu Thr Tyr Ser Ser Glu Val Pro Gly Ala Ala Val Gln Thr Met
              980                 985                 990

Ile Phe Asp Val Ile Ile Asp Arg  Glu Ser Pro Val Ile  Thr Thr Ala
         995                 1000                 1005

Thr Tyr  Asp Glu Thr Asn Phe  Thr Phe Asn Pro Arg  Pro Ala Ile
    1010                 1015                 1020

Glu Lys  Gly Glu Ser Gly Leu  Tyr Arg Glu Gln Val  Phe Tyr Leu
    1025                 1030                 1035

Val Ala  Asp Ala Ser Gly Val  Thr Thr Ile Pro Ser  Leu Leu Glu
    1040                 1045                 1050

Asn Gly  Asp Val Thr Val Ser  Asp Asn Lys Val Phe  Val Ala Gln
    1055                 1060                 1065

Asn Asp  Asp Gly Ser Phe Thr  Leu Pro Leu Asp Leu  Ala Asp Ile
    1070                 1075                 1080

Ser Lys  Phe Tyr Tyr Thr Val  Glu Asp Tyr Ala Gly  Asn Ile Ser
    1085                 1090                 1095

Tyr Glu  Lys Val Glu Asn Leu  Ile Ser Ile Gly Asn  Glu Lys Gly
    1100                 1105                 1110

Leu Val  Thr Val Asn Ile Leu  Asp Lys Asp Thr Asn  Ser Pro Val
    1115                 1120                 1125

Pro Ile  Leu Phe Ser Tyr Ser  Val Thr Asp Glu Thr  Gly Lys Ile
    1130                 1135                 1140

Val Ala  Glu Leu Pro Arg Tyr  Ala Gly Asp Thr Ser  Val Leu Lys
    1145                 1150                 1155

Leu Pro  Phe Gly Thr Tyr Thr  Phe Asp Leu Phe Leu  Tyr Asp Thr
    1160                 1165                 1170

Glu Trp  Ser Ser Leu Ala Gly  Glu Thr Lys Ala Val  Val Thr Ile
    1175                 1180                 1185

Leu Glu  Asp Asn Ser Thr Ala  Glu Val Asn Phe Tyr  Val Thr Leu
    1190                 1195                 1200

Lys Asp  Lys Ala Asn Leu Leu  Ile Asp Ile Asp Ala  Leu Leu Pro
    1205                 1210                 1215

Ser Gly  Ser Thr Ile Gln Leu  Val Thr Ala Asp Gly  Gln Ala Ile
    1220                 1225                 1230

Gln Leu  Pro Asn Ala Lys Tyr  Ser Lys Thr Asp Tyr  Gly Lys Phe
    1235                 1240                 1245

Val Pro  Val Gly Thr Tyr Thr  Ile Leu Pro Thr Leu  Pro Glu Gly
    1250                 1255                 1260

Tyr Glu  Phe Leu Glu Glu Leu  Asp Val Ala Val Leu  Ala Asn Gln
    1265                 1270                 1275

Ser Asn  Val Lys Lys Leu Thr  Leu Ile Asn Lys Val  Ala Leu Lys
```

-continued

```
          1280                1285                1290

Glu Leu  Ile Ala Glu Leu Ala  Gly Leu Glu Glu Thr  Ala Arg Tyr
    1295                1300                1305

Tyr Asn  Ala Ser Pro Glu Leu  Gln Thr Ala Tyr Ala  Lys Ala Leu
    1310                1315                1320

Glu Asp  Ala Asn Ala Val Tyr  Ala Asn Lys His Asn  Gln Ala Gln
    1325                1330                1335

Val Asp  Ser Ala Leu Ala Ser  Leu Val Ala Ala Arg  Glu Gln Leu
    1340                1345                1350

Asn Gly  Gln Ala Thr Asp Lys  Glu Lys Leu Ile Ala  Glu Val Ser
    1355                1360                1365

Asn Tyr  Thr Pro Thr Gln Ala  Asn Phe Ile Tyr Tyr  Asn Ala Glu
    1370                1375                1380

Asn Thr  Lys Gln Ile Ala Tyr  Asp Thr Ala Val Arg  Ser Ala Gln
    1385                1390                1395

Leu Val  Leu Asn Gln Glu Asn  Val Thr Gln Ala Val  Val Asn Gln
    1400                1405                1410

Ala Leu  Ala Asp Leu Leu Ala  Ala Lys Ala Asn Leu  Asp Gly Gln
    1415                1420                1425

Lys Thr  Asp Ile Ser Ala Leu  Arg Ser Ala Val Ser  Val Ser Ser
    1430                1435                1440

Val Leu  Lys Ala Thr Asp Ala  Lys Tyr Leu Asn Ala  Ser Glu Asn
    1445                1450                1455

Val Lys  Gln Ala Tyr Asp Gln  Ala Val Glu Ala Ala  Lys Ala Ile
    1460                1465                1470

Leu Val  Asp Glu Ser Ala Ser  Gln Ala Ser Val Asp  Gln Ala Leu
    1475                1480                1485

Ala Val  Leu Thr Ser Ala Gln  Ala Glu Leu Asp Gly  Val Ala Thr
    1490                1495                1500

Ser Thr  Asn Asp Ala Lys Glu  Pro Ala Asn Thr Ala  Thr Asp Lys
    1505                1510                1515

Lys Asp  Glu Gly Thr Val Thr  Pro Pro Pro Ile Asp  Ser Glu Ile
    1520                1525                1530

Val Asp  Val Gln Ala Pro Pro  Val Lys Asp Thr Gly  Asn Ser Glu
    1535                1540                1545

His Val  Pro Ile Gly Gln Lys  Pro Asn Pro Gln Pro  Thr Leu Pro
    1550                1555                1560

Arg Pro  Val Thr Leu Gln Ala  Ser Leu Ser Ser Pro  Asn Gln Glu
    1565                1570                1575

Lys Gln  Val Thr Gln Leu Pro  Asn Thr Gly Glu Asn  Asp Thr Lys
    1580                1585                1590

Tyr Tyr  Leu Val Pro Gly Val  Ile Ile Gly Leu Gly  Thr Leu Leu
    1595                1600                1605

Val Ser  Ile Arg Arg His Lys  Glu Glu Val
    1610                1615
```

```
<210> SEQ ID NO 10
<211> LENGTH: 408
<212> TYPE: PRT
<213> ORGANISM: Lactococcus lactis

<400> SEQUENCE: 10

Met Ala Lys Ala Asn Ile Gly Lys Leu Leu Leu Thr Gly Val Val Gly
1               5                   10                  15
```

-continued

```
Gly Ala Ile Ala Leu Gly Gly Ser Ala Ile Tyr Gln Ser Thr Thr Asn
            20                  25                  30

Gln Ser Ala Asn Asn Ser Arg Ser Asn Thr Thr Ser Thr Lys Val Ser
            35                  40                  45

Asn Val Ser Val Asn Val Asn Thr Asp Val Thr Ser Ala Ile Lys Lys
            50                  55                  60

Val Ser Asn Ser Val Val Ser Val Met Asn Tyr Gln Lys Asp Asn Ser
65                  70                  75                  80

Gln Ser Ser Asp Phe Ser Ser Ile Phe Gly Gly Asn Ser Gly Ser Ser
                85                  90                  95

Ser Ser Thr Asp Gly Leu Gln Leu Ser Ser Glu Gly Ser Gly Val Ile
            100                 105                 110

Tyr Lys Lys Ser Gly Gly Asp Ala Tyr Val Val Thr Asn Tyr His Val
            115                 120                 125

Ile Ala Gly Asn Ser Ser Leu Asp Val Leu Leu Ser Gly Gly Gln Lys
            130                 135                 140

Val Lys Ala Ser Val Val Gly Tyr Asp Glu Tyr Thr Asp Leu Ala Val
145                 150                 155                 160

Leu Lys Ile Ser Ser Glu His Val Lys Asp Val Ala Thr Phe Ala Asp
                165                 170                 175

Ser Ser Lys Leu Thr Ile Gly Glu Pro Ala Ile Ala Val Gly Ser Pro
                180                 185                 190

Leu Gly Ser Gln Phe Ala Asn Thr Ala Thr Glu Gly Ile Leu Ser Ala
            195                 200                 205

Thr Ser Arg Gln Val Thr Leu Thr Gln Glu Asn Gly Gln Thr Thr Asn
            210                 215                 220

Ile Asn Ala Ile Gln Thr Asp Ala Ala Ile Asn Pro Gly Asn Ser Gly
225                 230                 235                 240

Gly Ala Leu Ile Asn Ile Glu Gly Gln Val Ile Gly Ile Thr Gln Ser
                245                 250                 255

Lys Ile Thr Thr Thr Glu Asp Gly Ser Thr Ser Val Glu Gly Leu Gly
            260                 265                 270

Phe Ala Ile Pro Ser Asn Asp Val Val Asn Ile Ile Asn Lys Leu Glu
            275                 280                 285

Ala Asp Gly Lys Ile Ser Arg Pro Ala Leu Gly Ile Arg Met Val Asp
            290                 295                 300

Leu Ser Gln Leu Ser Thr Asn Asp Ser Ser Gln Leu Lys Leu Pro Ser
305                 310                 315                 320

Ser Val Thr Gly Gly Val Val Val Tyr Ser Val Gln Ser Gly Leu Pro
                325                 330                 335

Ala Ala Ser Ala Gly Leu Lys Ala Gly Asp Val Ile Thr Lys Val Gly
            340                 345                 350

Asp Thr Ala Val Thr Ser Ser Thr Asp Leu Gln Ser Ala Leu Tyr Ser
            355                 360                 365

His Asn Ile Asn Asp Thr Val Lys Val Thr Tyr Tyr Arg Asp Gly Lys
            370                 375                 380

Ser Asn Thr Ala Asp Val Lys Leu Ser Lys Ser Thr Ser Asp Leu Glu
385                 390                 395                 400

Thr Ser Ser Pro Ser Ser Ser Asn
                405
```

<210> SEQ ID NO 11
<211> LENGTH: 1902
<212> TYPE: PRT

-continued

```
<213> ORGANISM: Lactococcus lactis

<400> SEQUENCE: 11

Met Gln Arg Lys Lys Lys Gly Leu Ser Ile Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
            35                  40                  45

Thr Ala Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Ile Leu Arg Thr
                100                 105                 110

Asp Tyr Ser Ser Thr Ala Glu Ile Gln Gln Glu Thr Asn Lys Val Ile
            115                 120                 125

Ala Ala Gln Ala Ser Val Lys Ala Ala Val Glu Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
            195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Thr Val Lys His Gly Arg Tyr Phe Asn
                245                 250                 255

Ser Lys Val Pro Tyr Gly Phe Asn Tyr Ala Asp Asn Asn Asp Thr Ile
                260                 265                 270

Thr Asp Asp Lys Val Asp Glu Gln His Gly Met His Val Ala Gly Ile
            275                 280                 285

Ile Gly Ala Asn Gly Thr Gly Asp Asp Pro Ala Lys Ser Val Val Gly
    290                 295                 300

Val Ala Pro Glu Ala Gln Leu Leu Ala Met Lys Val Phe Ser Asn Ser
305                 310                 315                 320

Asp Thr Ser Ala Lys Thr Gly Ser Ala Thr Val Val Ser Ala Ile Glu
                325                 330                 335

Asp Ser Ala Lys Ile Gly Ala Asp Val Leu Asn Met Ser Leu Gly Ser
            340                 345                 350

Asn Ser Gly Asn Gln Thr Leu Glu Asp Pro Glu Leu Ala Ala Val Gln
            355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400
```

```
Leu Gln Asp Asn Glu Met Val Gly Ser Pro Gly Thr Ser Arg Gly Ala
            405                 410                 415

Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
            435                 440                 445

Leu Ser Ser His Asp Phe Thr Gly Ser Phe Asp Gln Lys Lys Phe Tyr
        450                 455                 460

Ile Val Lys Asp Ala Ser Gly Asn Leu Ser Lys Gly Ala Leu Ala Asp
465                 470                 475                 480

Tyr Thr Ala Asp Ala Lys Gly Lys Ile Ala Ile Val Lys Arg Gly Glu
                485                 490                 495

Phe Ser Phe Asp Asp Lys Gln Lys Tyr Ala Gln Ala Ala Gly Ala Ala
            500                 505                 510

Gly Leu Ile Ile Val Asn Thr Asp Gly Thr Ala Thr Pro Met Thr Ser
            515                 520                 525

Ile Ala Leu Thr Thr Thr Phe Pro Thr Phe Gly Leu Ser Ser Val Thr
            530                 535                 540

Gly Gln Lys Leu Val Asp Trp Val Thr Ala His Pro Asp Asp Ser Leu
545                 550                 555                 560

Gly Val Lys Ile Thr Leu Ala Met Leu Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
            595                 600                 605

Asn Asn Asn Gly Tyr Thr Asn Met Ser Gly Thr Ser Met Ala Ser Pro
        610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
            675                 680                 685

Gly Leu Val Asp Val Lys Ala Ala Ile Asp Ala Leu Glu Lys Asn Pro
        690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
                740                 745                 750

Val Tyr Thr Ser Ala Thr Asp Pro Asn Ser Gly Val Leu Tyr Asp Lys
            755                 760                 765

Lys Ile Asp Gly Ala Ala Ile Lys Ala Gly Ser Asn Ile Thr Val Pro
        770                 775                 780

Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
```

-continued

```
                  820               825               830
Asn Asp Gly Lys Ile Val Asp Ser Leu Asn Gly Ile Thr Tyr Ser Pro
          835               840               845
Ala Gly Gly Asn Phe Gly Thr Val Pro Leu Leu Lys Asn Lys Asn Thr
    850               855               860
Gly Thr Gln Tyr Tyr Gly Gly Met Val Thr Asp Ala Asp Gly Asn Lys
865               870               875               880
Thr Val Asp Asp Gln Ala Ile Ala Phe Ser Ser Asp Lys Asn Ala Leu
              885               890               895
Tyr Asn Asp Ile Ser Met Lys Tyr Tyr Leu Leu Arg Asn Ile Ser Asn
          900               905               910
Val Gln Val Asp Ile Leu Asp Gly Gln Gly Asn Lys Val Thr Thr Leu
          915               920               925
Ser Ser Ser Thr Asn Arg Lys Lys Thr Tyr Tyr Asn Ala His Ser Gln
    930               935               940
Gln Tyr Ile Tyr Tyr Asn Ala Pro Ala Trp Asp Gly Thr Tyr Tyr Asp
945               950               955               960
Gln Arg Asp Gly Asn Ile Lys Thr Ala Asp Asp Gly Ser Tyr Thr Tyr
              965               970               975
Arg Ile Ser Gly Val Pro Glu Gly Gly Asp Lys Arg Gln Val Phe Asp
          980               985               990
Val Pro Phe Lys Leu Asp Ser Lys  Ala Pro Thr Val Arg  His Val Ala
          995               1000              1005
Leu Ser  Ala Lys Thr Glu Asn  Gly Lys Thr Gln Tyr  Tyr Leu Thr
    1010              1015              1020
Ala Glu  Ala Lys Asp Asp Leu  Ser Gly Leu Asp Ala  Thr Lys Ser
    1025              1030              1035
Val Lys  Thr Glu Ile Asn Glu  Val Thr Asn Leu Asp  Ala Thr Phe
    1040              1045              1050
Thr Asp  Ala Gly Thr Thr Ala  Asp Gly Tyr Thr Lys  Ile Glu Thr
    1055              1060              1065
Pro Leu  Ser Asp Glu Gln Ala  Gln Ala Leu Gly Asn  Gly Asp Asn
    1070              1075              1080
Ser Ala  Glu Leu Tyr Leu Thr  Asp Asn Ala Ser Asn  Ala Thr Asp
    1085              1090              1095
Gln Asp  Ala Ser Val Gln Lys  Pro Gly Ser Thr Ser  Phe Asp Leu
    1100              1105              1110
Ile Val  Asn Gly Gly Gly Ile  Pro Asp Lys Ile Ser  Ser Thr Thr
    1115              1120              1125
Thr Gly  Tyr Glu Ala Asn Thr  Gln Gly Gly Gly Thr  Tyr Thr Phe
    1130              1135              1140
Ser Gly  Thr Tyr Pro Ala Ala  Val Asp Gly Thr Tyr  Thr Asp Ala
    1145              1150              1155
Gln Gly  Lys Lys His Asp Leu  Asn Thr Thr Tyr Asp  Ala Ala Thr
    1160              1165              1170
Asn Ser  Phe Thr Ala Ser Met  Pro Val Thr Asn Ala  Asp Tyr Ala
    1175              1180              1185
Ala Gln  Val Asp Leu Tyr Ala  Asp Lys Ala His Thr  Gln Leu Leu
    1190              1195              1200
Lys His  Phe Asp Thr Lys Val  Arg Leu Met Ala Pro  Thr Phe Thr
    1205              1210              1215
Asp Leu  Lys Phe Asn Asn Gly  Ser Asp Gln Thr Ser  Glu Ala Thr
    1220              1225              1230
```

-continued

```
Ile Lys Val Thr Gly Thr Val  Ser Ala Asp Thr Lys  Thr Val Asn
    1235              1240              1245

Val Gly His Thr Val Ala Ala  Leu Asp Ala Gln His  His Phe Ser
    1250              1255              1260

Val Asp Val Pro Val Asn Tyr  Gly Asp Asn Thr Ile  Lys Val Thr
    1265              1270              1275

Ala Thr Asp Lys Asp Gly Asn  Thr Thr Thr Glu Gln  Lys Thr Ile
    1280              1285              1290

Thr Ser Ser Tyr Asp Pro Asp  Met Leu Lys Lys Ser  Val Thr Phe
    1295              1300              1305

Asp Gln Gly Val Lys Phe Gly  Thr Asn Lys Phe Asn  Ala Thr Ser
    1310              1315              1320

Ala Lys Phe Tyr Asp Pro Lys  Thr Gly Ile Ala Thr  Ile Thr Gly
    1325              1330              1335

Lys Val Lys His Pro Thr Thr  Thr Leu Gln Val Asp  Gly Lys Gln
    1340              1345              1350

Ile Pro Ile Lys Asp Asp Leu  Thr Phe Ser Phe Thr  Leu Asp Leu
    1355              1360              1365

Gly Thr Leu Gly Gln Lys Pro  Phe Gly Val Val Val  Gly Asp Thr
    1370              1375              1380

Thr Gln Asn Lys Thr Phe Gln  Glu Ala Leu Ser Phe  Ile Leu Asp
    1385              1390              1395

Ala Val Ala Pro Thr Leu Ser  Leu Asp Ser Ser Thr  Asp Ala Pro
    1400              1405              1410

Val Tyr Thr Asn Asp Pro Asn  Phe Gln Ile Thr Gly  Thr Ala Thr
    1415              1420              1425

Asp Asn Ala Gln Tyr Leu Ser  Leu Ser Ile Asn Gly  Ser Ser Val
    1430              1435              1440

Ala Ser Gln Tyr Glu Asp Ile  Asn Ile Asn Ser Gly  Lys Pro Gly
    1445              1450              1455

His Met Ala Ile Asp Gln Pro  Val Lys Leu Leu Glu  Gly Lys Asn
    1460              1465              1470

Val Leu Thr Val Ala Val Thr  Asp Ser Glu Asp Asn  Thr Thr Thr
    1475              1480              1485

Lys Asn Ile Thr Val Tyr Tyr  Glu Pro Lys Lys Thr  Leu Ala Ala
    1490              1495              1500

Pro Thr Val Thr Pro Ser Thr  Thr Glu Pro Ala Gln  Thr Val Thr
    1505              1510              1515

Leu Thr Ala Asn Ala Ala Ala  Thr Gly Glu Thr Val  Gln Tyr Ser
    1520              1525              1530

Ala Asp Gly Gly Lys Thr Tyr  Gln Asp Val Pro Ala  Ala Gly Val
    1535              1540              1545

Thr Ile Thr Ala Asn Gly Thr  Phe Lys Phe Lys Ser  Thr Asp Leu
    1550              1555              1560

Tyr Gly Asn Glu Ser Pro Ala  Val Asp Tyr Val Val  Thr Asn Ile
    1565              1570              1575

Lys Ala Asp Asp Pro Ala Gln  Leu Gln Ala Ala Lys  Gln Glu Leu
    1580              1585              1590

Thr Asn Leu Ile Ala Ser Ala  Lys Thr Leu Ser Ala  Ser Gly Lys
    1595              1600              1605

Tyr Asp Asp Ala Thr Thr Thr  Ala Leu Ala Ala Ala  Thr Gln Lys
    1610              1615              1620
```

-continued

```
Ala Gln  Thr Ala Leu Asp Gln  Thr Asn Ala Ser Val  Asp Ser Leu
    1625              1630              1635

Thr Gly  Ala Asn Arg Asp Leu  Gln Thr Ala Ile Asn  Gln Leu Ala
    1640              1645              1650

Ala Lys  Leu Pro Ala Asp Lys  Lys Thr Ser Leu Leu  Asn Gln Leu
    1655              1660              1665

Gln Ser  Val Lys Asp Ala Leu  Gly Thr Asp Leu Gly  Asn Gln Thr
    1670              1675              1680

Asp Pro  Ser Thr Gly Lys Thr  Phe Thr Ala Ala Leu  Asp Asp Leu
    1685              1690              1695

Val Ala  Gln Ala Gln Ala Gly  Thr Gln Thr Asp Asp  Gln Leu Gln
    1700              1705              1710

Ala Thr  Leu Ala Lys Ile Leu  Asp Glu Val Leu Ala  Lys Leu Ala
    1715              1720              1725

Glu Gly  Ile Lys Ala Ala Thr  Pro Ala Glu Val Gly  Asn Ala Lys
    1730              1735              1740

Asp Ala  Ala Thr Gly Lys Thr  Trp Tyr Ala Asp Ile  Ala Asp Thr
    1745              1750              1755

Leu Thr  Ser Gly Gln Ala Ser  Ala Asp Ala Ser Asp  Lys Leu Ala
    1760              1765              1770

His Leu  Gln Ala Leu Gln Ser  Leu Lys Thr Lys Val  Ala Ala Ala
    1775              1780              1785

Val Glu  Ala Ala Lys Thr Val  Gly Lys Gly Asp Gly  Thr Thr Gly
    1790              1795              1800

Thr Ser  Asp Lys Gly Gly Gly  Gln Gly Thr Pro Ala  Pro Ala Pro
    1805              1810              1815

Gly Asp  Thr Gly Lys Asp Lys  Gly Asp Glu Gly Ser  Gln Pro Ser
    1820              1825              1830

Ser Gly  Gly Asn Ile Pro Thr  Lys Pro Ala Thr Thr  Thr Ser Thr
    1835              1840              1845

Thr Thr  Asp Asp Thr Thr Asp  Arg Asn Gly Gln Leu  Thr Ser Gly
    1850              1855              1860

Lys Gly  Ala Leu Pro Lys Thr  Gly Glu Thr Thr Glu  Arg Pro Ala
    1865              1870              1875

Phe Gly  Phe Leu Gly Val Ile  Val Val Ser Leu Met  Gly Val Leu
    1880              1885              1890

Gly Leu  Lys Arg Lys Gln Arg  Glu Glu
    1895              1900
```

```
<210> SEQ ID NO 12
<211> LENGTH: 1236
<212> TYPE: DNA
<213> ORGANISM: Streptococcus thermophilus

<400> SEQUENCE: 12
atgaaaaaaa ttaactggaa gaaaatagtc gcgccaattg caatgctaat tattggctta       60
ctaggtggtt tacttggtgc ctttatccta ctaacagcag ccggggtatc ttttaccaat      120
acaacagata ctggagcaaa aacggctaag accgtctaca ccaatataac agatacaact      180
aaggctgtta agaagtaca aaatgccgtt gtttctgtca tcaattatca agaaggttca      240
tcttcagatt ctctaaatga cctttatggc cgtatctttg gcggagggga cagttctgat      300
tctagccaag aaaattcaaa agattcagat ggcctgcagg tcgctggtga aggttctgga      360
gtcatctata aaaagatgg caaagaagcc tacatcgtaa ccaataacca cgttgtcgat      420
```

| ggggctaaaa aactcgaaat catgctttcg gatggttcga aaattactgg tgaacttgtt | 480 |

| ggtaaagaca cttactctga cctagcagtt gtcaaagtat cttcagataa aataacaact | 540 |

| gttgcagaat ttgcagactc aaactccctt actgttggtg aaaaagcaat tgctattggt | 600 |

| agcccacttg gtaccgaata cgccaactca gtaacagaag aatcgtttc tagccttagc | 660 |

| cgtactataa cgatgcaaaa cgataatggt gaaactgtat caacaaacgc tatccaaaca | 720 |

| gatgcagcca ttaaccctgg taactctggt ggtgccctag tcaatattga aggacaagtt | 780 |

| atcggtatta actcaagtaa aatttcatca acgtctgcag tcgctggtag tgctgttgaa | 840 |

| ggtatggggt ttgccattcc atcaaacgat gttgttgaaa tcatcaatca attagaaaaa | 900 |

| gatggtaaag ttacacgacc agcactaggg atctcaatag cagatcttaa tagcctttct | 960 |

| agcagcgcaa cttctaaatt agatttacca gatgaggtca aatccggtgt tgttgtcggt | 1020 |

| agtgttcaga aaggtatgcc agctgacggt aaacttcaag aatatgatgt tatcactgag | 1080 |

| attgatggta agaaaatcag ctcaaaaact gatattcaaa ccaatcttta cagccatagt | 1140 |

| atcggagata ctatcaaggt aaccttctat cgtggtaaag ataagaaaac tgtagatctt | 1200 |

| aaattaacaa aatctacaga agacatatct gattaa | 1236 |

```
<210> SEQ ID NO 13
<211> LENGTH: 1227
<212> TYPE: DNA
<213> ORGANISM: Lactococcus lactis

<400> SEQUENCE: 13
```

| atggcaaaag ctaatatagg aaaattgcta ttaacaggtg tcgtgggcgg agccatcgca | 60 |

| cttggaggaa gtgcaatcta tcaaagcact acaaatcaat cggcaaataa tagtcgttca | 120 |

| aatacaacta gtacaaaggt tagtaacgtt tcggtaaatg tcaataccga tgttacctct | 180 |

| gcaattaaaa aagtttcaaa ttctgtcgtt tctgttatga attatcaaaa agataactca | 240 |

| caaagtagtg acttcagttc aatttttggt ggaaatagcg gttcaagttc atcgactgat | 300 |

| ggcttacagc tttctagtga aggctctggt gtcatctaca aaaaatctgg tggtgatgcc | 360 |

| tacgttgtaa ctaactacca cgttattgct ggtaatagct cacttgatgt tctgcttct | 420 |

| ggtggacaaa aagtcaaagc ttctgtggtt ggttatgatg aatacacaga ccttgctgtt | 480 |

| cttaaaatca gttctgaaca tgtcaaagat gtggcgacat cgctgattc tagtaaatta | 540 |

| acaattggtg aacctgccat tgccgttggc tcacctttag gtagtcaatt tgcaaacacc | 600 |

| gcaactgaag aattttatc tgcaacaagc cgtcaagtga ctttgaccca agaaaatggt | 660 |

| caaacaacta atatcaatgc aattcaaaca gatgctgcca ttaaccctgg taactctgga | 720 |

| ggggctttga ttaatattga aggacaagtt attggaatta ctcaaagtaa aattacaaca | 780 |

| actgaagatg gttctacttc tgtcgaaggt ttaggatttg cgattccttc taatgatgtc | 840 |

| gtaaatatca ttaataaact tgaagctgat ggtaagagtt cacgccctgc tttaggtatc | 900 |

| cgaatggttg accttttcaca attatcaaca aatgacagtt ctcaattgaa attaccaagc | 960 |

| agtgtaacag gtggggttgt tgtttactcc gtccaatctg gacttcctgc tgcctcagct | 1020 |

| ggtttgaaag ctggagatgt aattacaaag gttggcgata cagcagtaac ctcttcaaca | 1080 |

| gacttgcaaa gtgctcttta ctcacacaat atcaatgata cagtaaaagt tacttattat | 1140 |

| cgtgatggta aatcaaatac agcagatgtt aaactttcta aatcaaccag tgacttagaa | 1200 |

| acaagcagtc catcttcttc taattaa | 1227 |

-continued

```
<210> SEQ ID NO 14
<211> LENGTH: 4856
<212> TYPE: DNA
<213> ORGANISM: Streptococcus thermophilus

<400> SEQUENCE: 14 atgaaaaga aagaaacttt ctcacttcgg aagtataaaa ttggaactgt gtctgttctt      60
ttgggtgcag ttttttttgtt tgcaggtgca ccatcggtag ctgcagatga attgacaagc    120
cttgtagaga ctaaggtgga agcaactgtt cctgacgcaa tcgtcagcga atcagcctca     180
gaaagtcccg tagccgagga gttggttgac acttctgtgg aggctacctc aactgatgta     240
accactacag ataatgaaga ggaaacactt ggctcagaaa gtcccgtagt cgaggagttg      300
gttgacactt ctgtggaggc taccccaact gatgtaacca ctacagataa tgtagaggaa     360
acacttggct cagaagctct tgaaaacatc acaaatacag aagtagaagc gactcaacca     420
gctgtagaaa ctccagctat ttcagagaaa aaagtagaag aagaggagaa gctttccgta     480
gcagatgaga ctactgctat tactaatcag gaagaagcga aaccacaaaa cattgatagt     540
aatacaatca ttacagtacc taaagtttgg gatagtggtt acaagggcga aggaacagta     600
gttgcaatca tagattccgg tcttgacgtt gaccacgatg tattgcatat ttcagatctc     660
tcaaccgcaa aatataaatc agaaaaagag atagaagcag ctaaagaagt agcaggaatt     720
tcctacggtg aatggtttaa cgataaggtt gtatttggtt ataactatgt tgatgtgaat     780
actgtcttga agaagaaga caaacgctca cacggtatgc acgtaacgag tattgccaca      840
ggaaatccga cacaaccagt cgctggacaa ttaatgtatg gtgtagctcc tgaagcgcaa     900
gtcatgttta tgcgtgtatt ctcagacctc aaagctacaa caggcgcagc attgtatgta     960
aaggcgattg aagatgctgt aaaattaggt gcagatagca tcaacctcag cctgggagga    1020
gctaacggct ctgttgttaa catgaatgaa aatgtgactg cagcaatcga ggctgctcgt    1080
cgtgcagggg tttctgttgt tattgcagct ggtaatgatg gaacatttgg ttcaggtcat    1140
tctaatccgt cagccgatta tccagattat ggcttggtcg gtgcaccttc aacagctcgc    1200
gatgcaattt ctgtcgcttc ttacaataac acaacggttg gtagtaaagt aatcaatatc    1260
attggcttag aaaacaatgc tgacttgaat tacggtaaga gttcgtttga taatccagag    1320
aaaagtccgg taccatttga aatcgggaaa gaatatgaat atgtttatgc gggaatcggt    1380
caagcttcgg attttgatgg tctagatttg actggaaaac ttgcacttat taaacgagga    1440
accatcagtt tctcagaaaa aatagccaat gcaacagctg caggtgcagt aggggtggtc    1500
attttcaata gccgtccaga tgaagccaat gtaagcatgc aacttgatga tacagctatt    1560
gcaattccat ctgtcttcat tccattggaa tttggtgaag ctttggcagc taactcatat    1620
aagattgcgt tcaataacga aacagacatt cgtcctaacc cagaagcagg tcttctttca    1680
gatttttcaa gttgggggtct atcagcggat ggcgagctaa aaccagactt agctgctcca    1740
ggtggtgcta tttatgcagc catcaatgat aatgactatg ccaatatgca gggaacaagt    1800
atggcttcac cacacgtagc aggagcagcc gtactagtaa aacaatattt acaggcaact    1860
taccctacta gtcccctca agaaatcgaa gccttagtaa aacacttgct tatgtctact    1920
gctaaagcac atgtgaacaa agaaacaaca gcctacactt cccctcgcca acaaggtgca    1980
ggtatcatcg atactgcagc agcgatttct acaggtttat atttgactgg cgaagacggt    2040
tatggcagca ttactttggg aaatgttgaa gatacattca gctttacggt cacacttcat    2100
aacattacaa acgaagataa gactttaaac tactcaacgc aattaacaac tgatactgtc    2160
```

-continued

```
caaaacggat tgatcacctt ggctccgcgt ctattagctg agattcctgg cggtaaggtg    2220
actgtgcaag ccaattcaag tacaactgtt acaattaatg tcgatgcatc aagctttgca    2280
gaagaattga caggtttaat gaaaaacggt tactatcttg aaggttttgt tcgatttaca    2340
gatgtagccg atggcggtga tattgtcagc attccataca ttggtttccg tggggaattc    2400
caaaatctag ccgttctaga agagccgatt tacaatctta ttgccgatgg taaggggggc    2460
ttctactttg aacctgttac agcacaacca gatagtgttg acatcagcca tcactacaca    2520
ggtcttgtta caggaagtac ggagttaatc tattctacag acaaacgatc tgactttgcg    2580
atcaagaaga ctctaggtac atttaaaaat gaagcaggat actttgtttt agagcttgat    2640
gagtctggta aacctcattt agctatctcg ccaaatgggg atgacaacca agattcgctc    2700
gctttcaaag gtgtcttctt gagaaattat acggatttag tcgcaagcgt ctatgctgca    2760
gatgatactg agcgaacaaa tccactttgg gaaagtcaac cacagtcagg caataagaac    2820
ttctatagtg gtgatcctaa aaatccaaaa tcaagcatta tttaccctac tgaatggaat    2880
gggacagaca gcgagggaaa tgctttagca gatggtaagt atcaatacgt tttgacctac    2940
tcatctgaag ttccaggtgc agcagtacaa actatgattt tcgatgttat catcgataga    3000
gaatcaccag ttatcaccac agctacctat gatgaaacaa actttacatt taaccctcgt    3060
ccagccattg aaaaaggaga atccggtcta tatcgcgagc aagtattcta ccttgtagca    3120
gatgcaagcg gtgtgacaac tattccttcc ttattagaaa atggagatgt aaccgtttct    3180
gataacaagg tatttgtggc acaaaacgac gatggctcct ttacattgcc tcttgatctt    3240
gcagatattt caaaattcta ctacacagta gaggattatg ctggtaacat cagctatgaa    3300
aaagtagaga atctgatcag tattggcaat gaaaaagggt tggtaactgt caatattctt    3360
gataaagata caaatagtcc tgtaccaata cttttctctt actcagtcac cgatgaaaca    3420
ggcaagattg ttgcagaatt accacgatat gccggcgata ctagcgttct taagctacca    3480
tttggtactt acacctttga tttattctta tatgatacag agtggtcaag cctagcaggt    3540
gaaacaaaag cagtcgtgac gattttggaa gataatagca ctgccgaggt gaatttctat    3600
gtgactttga aagataaggc taacttgctg atagatattg atgcattact accttctggt    3660
tcaaccatcc aactggtaac tgctgatggt caggctattc agctaccaaa tgctaaatat    3720
tctaagacta ttattggtaa atttgtacca gttggtacct acactatcct tccaaccctc    3780
ccagaaggct atgaatttttt ggaagaatta gacgtagcag tacttgcaaa ccagtcaaat    3840
gttaagaaat taaccttgat taataaagtt gctttgaaag aactgattgc tgaacttgca    3900
ggacttgaag aaacagcgcg ttattacaat gctagtccag aacttcaaac tgcctatgct    3960
aaagcattag aagatgccaa tgcagtatat gccaataaac acaatcaggc acaagtagat    4020
tcagcacttg ccagtcttgt ggcggcgaga gaacagctaa acggtcaggc taccgataag    4080
gaaaaactaa ttgctgaagt atcaaactac acaccgactc aggcaaactt tatttattac    4140
aatgctgaaa ataccaaaca aattgcctat gatacagctg ttcgttcagc acaacttgta    4200
ttgaaccaag agaatgtaac tcaggcagtt gtcaaccaag cgttggctga cttgttagca    4260
gcgaaagcca acttagatgg tcaaaagact gatatttcag cccttcgtag cgcagtatct    4320
gtttcttccg tattaaaagc gacagatgct aagtatctca atgcatctga gaacgtgaaa    4380
caagcttatg accaggcagt tgaagcagcg aaagcgattc tagttgatga atctgcaagc    4440
caagcaagtg tcgatcaagc tctagccgtt ctgacaagcg ctcaggcaga actggatggt    4500
gttgctactt caacaaatga tgccaaagag ccagcaaata ctgccactga caaaaaagat    4560
```

-continued

```
gaaggcactg taacgcctcc acctatagac tcagaaatag ttgatgtaca ggcacctcct    4620
gtaaaagata ctgggaattc agagcatgta ccgataggtc agaagccaaa ccctcaacca    4680
actttacctc gtccagtcac tttgcaagct agtctatcta gtcctaatca agaaaaacag    4740
gtgactcaac taccaaatac tggagaaaat gatacgaaat actatcttgt tcctggtgtc    4800
attattgggc tagggactct gttggtaagc atacgacgtc acaaggaaga agtata        4856
```

<210> SEQ ID NO 15
<211> LENGTH: 5889
<212> TYPE: DNA
<213> ORGANISM: Lactococcus lactis

<400> SEQUENCE: 15

```
atgcaaagga aaaagaaagg gctatcgatc ttgttagccg gtacagtcgc tttaggggcg      60
ctggctgtct tgccagtcgg cgaaatccaa gcaaaggcgg ctatctcgca gcaaactaag     120
ggatcatcac tcgcaaatac ggtgacggct gcgactgcta agcaagcggc cactgacaca     180
actgcagcga caacgaatca agcgattgct acacagttgg cggctaaagg tattgattac     240
aataagctga ataaagttca gcagcaagat atttatgttg acgtcattgt tcaaatgagc     300
gcagcgcctg cctctgaaaa cggcacttta agaactgatt actccagcac ggcggagatt     360
cagcaggaga ccaataaagt gatcgcggct caggcaagcg ttaaagcagc tgttgaacaa     420
gtcacccaac aaactgccgg tgaaagttat ggctatgtcg ttaacggctt ttcaactaaa     480 gttaggggttg ttgatatccc taaactgaaa caaattgccg gagttaaaac agtcacattg     540
gcgaaagttt attatccgac tgatgctaag gcaaactcga tggcgaatgt gcaagccgta     600
tggtccaatt acaaatataa aggtgaaggc acagttgtct cggttattga cagtggcatt     660
gatccaacac ataaagacat gcggctaagc gatgataaag acgttaaact aaccaaatct     720
gatgttgaaa aattcactga taccgccaag catggccgct attttaattc aaaagtgcca     780
tatgggttta attacgctga taataacgac accattacag atgatacggt tgacgaacaa     840
cacggcatgc atgttgctgg gatcatcggt gctaacggga caggtgacga tccagccaag     900
tctgttgtcg gagttgcgcc agaagcacag ctactggcaa tgaaagtttt caccaactct     960
gacacttctg caacaaccgg gtcagctacc ttggtttctg ccattgaaga ctcggcaaaa    1020
atcggtgccg atgtcctcaa catgtcctta ggatctgatt caggcaacca aaccttggag    1080
gatccagaac ttgctgcggt gcaaaatgct aacgaatcag gaacagccgc cgtcatttct    1140
gctgggaact caggaacatc cggttcagca actgaaggcg tcaacaaaga ttattacggt    1200
ttgcaagaca atgaaatggt gggatcgcca gggacatcac gaggagcgac cacagttgct    1260
tccgctgaaa acacggatgt catcactcag gcagtgacca ttacagatgg tacaggttta    1320
cagcttggac cggaaaccat tcagctttca agccacgatt tcactggtag ctttgaccaa    1380
aagaagtttt atattgttaa agatgctagt ggcaacctca gcaaaggggc attagccgac    1440
tatactgctg acgctaaagg caaaattgcc atcgttaaac gtggcgaatt tagctttgat    1500
gacaaacaaa aatacgccca agccgctggt gctgctggct tgatcattgt caacaccgat    1560
ggcacagcaa caccgatgac ttctattgcg ttaaccacca ccttcccaac atttgggctc    1620
tccagtgtaa ccggtcaaaa gctggttgac tgggtcacag cacacccgga tgatagtctc    1680
ggtgtcaaga ttaccctggc gatgttacca aatcagaaat atactgaaga caagatgtct    1740
gacttcacat cctatgggcc agtttccaat ctttccttca aaccagatat taccgcacca    1800
```

-continued

```
ggcggtaaca tctggtcaac gcaaaacaac aatggctaca caaatatgtc tggtacgtca      1860
atggcctcgc catttattgc cggttcacaa gcattgttga aacaagcatt gaataacaaa      1920
aacaacccat tttatgctta ctacaaacaa cttaaaggga cagcgctcac cgattttctt      1980
aagacagttg agatgaatac tgcccagcca atcaacgata ttaactacaa taatgttatc      2040
gtatcgccgc ggcggcaagg ggccggtctg gttgatgtga aggcagccat tgatgcatta      2100
gaaaagaatc cgtcaacggt tgtcgccgaa aacggctacc cggcagttga attgaaagac      2160
ttcacgagta cggacaagac ctttaaactc accttcacga atcgcacgac ccatgaacta      2220
acctatcaaa tggacagtaa tacggatact aatgccgttt atacatcagc gactgaccct      2280
aattctgggg ttttgtatga caagaagatt gatggagcag ccattaaagc tggcagtaac      2340
ataactgtgc ctgctgggaa aacggcgcag attgaattca cactatcttt gccgaagtct      2400
tttgaccaac agcaatttgt tgaaggtttt ctgaacttta agggtagcga tggatcgcgc      2460
ttgaacttgc catacatggg cttttttggt gactggaatg acggtaagat tgtcgatagt      2520
ctcaatggga tcacttatag tcctgctggt ggtaattttg gcaccgtgcc actattgaaa      2580
aacaaaaata caggcactca atattatggc ggcatggtca cagacgctga tggcaacaag      2640
acagttgacg atcaggcgat tgctttttcg agtgacaaga atgccttata taatgaaatc      2700
agcatgaagt attatctatt gcgcaatatc agcaacgtcc aagttgatat tcttgatggt      2760
cagggcaata aagttacgac tctcagcagt tccaccaatc ggaagaagac ctattataat      2820
gctcattcgc agcagtacat ctactacaat gctccagcgt gggatggcac ctattatgat      2880
caacgtgatg gcaacatcaa gacggctgat gatggcagtt atacttatcg tatttccggt      2940
gtaccggaag gcggcgacaa acgtcaagtg tttgatgtgc ctttcaagct cgactctaag      3000
gcgccgacag ttcgtcatgt cgctttgtca gccaaaacgg aaaatgggaa aacccagtat      3060
tatttgacag ctgaagccaa ggatgatttg agtggtcttg atgccaccaa gagcgttaaa      3120
actgaaatta atgaagtgac gaatcttgat gctacctta ccgatgctgg gacaacggct      3180
gatgggtaca ccaaaattga aacgccatta tctgatgaac aggcccaagc acttggcaat      3240
ggcgacaatt cggctgagct gtacttgact gataatgcat ccaatgccac tgatcaagat      3300
gccagcgttc agaagccggg gtctacatcg tttgatttaa ttgtgaacgg cggcggtatc      3360
ccagacaaga tctcaagtac cacaaccggc tacgaagcca atactcaagg tggcgggacg      3420
tatacgttta gtggaacgta tccagcagcg gttgacggta cttacactga tgcacaagga      3480
aagaaacatg atttgaacac aacctacgat gctgcgacta acagtttcac tgcctcaatg      3540
ccggtcacga atgctgatta cgccgcgcaa gtggatctat atgccgataa ggcgcatacc      3600
cagttgctta acattttga caccaaagtt cgactgacgg cgccaacctt tactgatttg      3660
aaattcaaca atggctcgga tcagacctct gaagcgacca tcaaggttac agggacggtt      3720
agtgctgaca ccaagacagt taatgttggc gacaccgtag cagcacttga tgcacaacat      3780
cactttagtg ttgatgtacc ggttaattat ggtgacaata ccatcaaggt gaccgccacc      3840
gacgaagatg gcaacaccac gacggagcaa aagacgatta cctcgtctta tgatcctgat      3900
atgttgaaga attctgtgac gttcgatcaa ggtgtgacat ttggtgccaa tgaattcaat      3960
gccacctcgg ctaagttcta tgaccctaag accgggattg cgacgattac tggtaaggtc      4020
aagcacccaa cgacaacgtt gcaggttgat ggtaagcaaa ttccaatcaa ggatgatctg      4080
actttcagtt tcactttaga tttaggtact cttggacaaa aacgtttggg ggttgttgtg      4140
ggtgacacca ctcaaaacaa gaccttccaa gaagcgttga ccttcatttt ggatgcagtg      4200
```

-continued

```
gctccaacat tgtcattgga cagctcgaca gatgcaccgg tttataccaa cgatccaaac    4260
ttccagatta ccggaacggc cactgacaat gcgcaatatc tgagtctgtc aattaacggc    4320
agttctgtcg ccagccaata cgtagacatc aacatcaata gtggcaaacc aggtcatatg    4380
gctattgatc agcccgttaa attgctcgaa ggcaaaaacg tgctgactgt tgctgttaca    4440
gatagcgaag acaacaccac gaccaagaac atcacagttt actacgaacc aaagaaaaca    4500
ctggcagcac caactgtgac gccaagtacc actgaaccag ccaaaacggt gactctgacg    4560
gcaaactctg ccgcaacggg cgaaacggtt cagtatagtg ctgatggtgg caagacatat    4620
caggatgttc cggcagccgg tgtcacggtc acggcaaatg gcaccttcaa gtttaagtcg    4680
actgatttat acggtaatga atcaccagcc gtcgactatg ttgtcaccaa tatcaaggcc    4740
gatgatcctg cacaattgca ggcagctaag caggaactga ctaatctgat tgcttccgcc    4800
aaaacgctaa gtgccagcgg taagtatgat gatgccacaa cgactgcttt agcagcggca    4860
acgcagaagg cacaaacggc gcttgatcag acgaacgcct cagttgattc acttactggt    4920
gccaatcgag acctgcaaac tgcgatcaat caattagctg ccaagttacc tgcagataag    4980
aagacttcgc tgcttaacca gttgcaatct gtgaaggctg cgctgggaac ggacttgggc    5040
aatcaaactg attcaagcac tggcaaaaca tttacggcag cgttagacga cctagtggca    5100
caagctcaag cagggacgca aacggacgac cagcttcaag cgactcttgc caaggtactt    5160
gatgcagtat tagcaaaact tgcggagggt attaaagcgg caacaccggc tgaggttggc    5220
aatgctaaag atgctgcaac tggcaaaact tggtatgccg acattgctga cacattgacg    5280
tctggtcaag ccagtgctga tgcgtctgac aagcttgcac atttacaagc tttgcaaagt    5340
ctgaaaacga aggtggcagc tgccgttgaa gcggccaaga cagttggtaa aggcgacggt    5400
acaaccggta ctagcgacaa aggcggcggt caaggtaccc cggcgcccgc tccaggcgac    5460
acaggtaagg acaaaggaga tgagggcagc cagcctagtt ctggcggtaa tatcccaaca    5520
aagccagcca caacgacgtc aacgaccacg gatgatacga ctgatcgtaa tggtcaactt    5580
acatccggta ctagcgacaa aggcggcggt caaggtaccc cggcgcccgc tccaggcgac    5640
ataggtaagg acaaaggcga tgagggcagc cagcctagtt ctggcggtaa tatcccaaca    5700
aatccagcca caacgacgtc aacgaccacg gatgatacga ctgatcgtaa tggtcaactt    5760
acatccggta agggagcatt acccaagaca ggagagacaa ctgagcggcc agcgtttggc    5820
ttcttgggtg tcattgtggt cagtctgatg ggggtattag gattgaaacg gaaacaacgt    5880
gaagaatag                                                          5889
```

<210> SEQ ID NO 16
<211> LENGTH: 19
<212> TYPE: DNA
<213> ORGANISM: Artificial Sequence
<220> FEATURE:
<223> OTHER INFORMATION: Synthesized primer

<400> SEQUENCE: 16

```
gtaatcacgg tcaccaacc                                                      19
```

<210> SEQ ID NO 17
<211> LENGTH: 53
<212> TYPE: DNA
<213> ORGANISM: Artificial Sequence
<220> FEATURE:
<223> OTHER INFORMATION: Synthesized primer -continued

<400> SEQUENCE: 17
gacatctaat cttttctgaa gtacatccgc aacagtaaac cacctagtaa gcc        53

<210> SEQ ID NO 18
<211> LENGTH: 56
<212> TYPE: DNA
<213> ORGANISM: Artificial Sequence
<220> FEATURE:
<223> OTHER INFORMATION: Synthesized primer

<400> SEQUENCE: 18
ataatcttac ctatcacctc aaatggttcg ctgggtagtg ttcagaaagg tatgcc      56

<210> SEQ ID NO 19
<211> LENGTH: 20
<212> TYPE: DNA
<213> ORGANISM: Artificial Sequence
<220> FEATURE:
<223> OTHER INFORMATION: Synthesized primer

<400> SEQUENCE: 19
ggattgagat ttgatcgttg                                              20

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
gttgcggatg tacttcag                                                18

<210> SEQ ID NO 21
<211> LENGTH: 17
<212> TYPE: DNA
<213> ORGANISM: Artificial Sequence
<220> FEATURE:
<223> OTHER INFORMATION: Synthesized primer

<400> SEQUENCE: 21
ccagcgaacc atttgag                                                 17

<210> SEQ ID NO 22
<211> LENGTH: 17
<212> TYPE: DNA
<213> ORGANISM: Artificial Sequence
<220> FEATURE:
<223> OTHER INFORMATION: Synthesized primer

<400> SEQUENCE: 22
tggtaagcac gtagacc                                                 17

<210> SEQ ID NO 23
<211> LENGTH: 53
<212> TYPE: DNA
<213> ORGANISM: Artificial Sequence
<220> FEATURE:
<223> OTHER INFORMATION: Synthesized primer

<400> SEQUENCE: 23
ctactgacag cttccaagga gctaaagagg tcccaggctt gtcaattcat ctg         53

<210> SEQ ID NO 24
<211> LENGTH: 52

```
<212> TYPE: DNA
<213> ORGANISM: Artificial Sequence
<220> FEATURE:
<223> OTHER INFORMATION: Synthesized primer

<400> SEQUENCE: 24
gcaagtcagc acgaacacga accgtcttat ctccgaaagc caacttagat gg          52

<210> SEQ ID NO 25
<211> LENGTH: 19
<212> TYPE: DNA
<213> ORGANISM: Artificial Sequence
<220> FEATURE:
<223> OTHER INFORMATION: Synthesized primer

<400> SEQUENCE: 25
cgtatgctta ccaacagag                                               19

<210> SEQ ID NO 26
<211> LENGTH: 21
<212> TYPE: DNA
<213> ORGANISM: Artificial Sequence
<220> FEATURE:
<223> OTHER INFORMATION: Synthesized primer

<400> SEQUENCE: 26
gggacctctt tagctccttg g                                            21

<210> SEQ ID NO 27
<211> LENGTH: 23
<212> TYPE: DNA
<213> ORGANISM: Artificial Sequence
<220> FEATURE:
<223> OTHER INFORMATION: Synthesized primer

<400> SEQUENCE: 27
ggagataaga cggttcgtgt tcg                                          23

<210> SEQ ID NO 28
<211> LENGTH: 21
<212> TYPE: DNA
<213> ORGANISM: Artificial Sequence
<220> FEATURE:
<223> OTHER INFORMATION: Synthesized primer

<400> SEQUENCE: 28
cccaacaaca ccaggctcat t                                            21

<210> SEQ ID NO 29
<211> LENGTH: 54
<212> TYPE: DNA
<213> ORGANISM: Artificial Sequence
<220> FEATURE:
<223> OTHER INFORMATION: Synthesized primer

<400> SEQUENCE: 29
gaaaaattct atagaaactt ctctcaatta ggctaaggct gatccggatg ccaa        54

<210> SEQ ID NO 30
<211> LENGTH: 54
<212> TYPE: DNA
<213> ORGANISM: Artificial Sequence
<220> FEATURE:
<223> OTHER INFORMATION: Synthesized primer

<400> SEQUENCE: 30
```

-continued

```
tacagattaa taattattct ttattataca gatccagagt aatttccagt tgcc          54

<210> SEQ ID NO 31
<211> LENGTH: 20
<212> TYPE: DNA
<213> ORGANISM: Artificial Sequence
<220> FEATURE:
<223> OTHER INFORMATION: Synthesized primer

<400> SEQUENCE: 31
ttcgaggcct acgcaatgcg                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthesized primer

<400> SEQUENCE: 32
gatctgtata ataaagaata                                                 20

<210> SEQ ID NO 33
<211> LENGTH: 21
<212> TYPE: DNA
<213> ORGANISM: Artificial Sequence
<220> FEATURE:
<223> OTHER INFORMATION: Synthesized primer

<400> SEQUENCE: 33
agcctaattg agagaagttt c                                               21

<210> SEQ ID NO 34
<211> LENGTH: 19
<212> TYPE: DNA
<213> ORGANISM: Artificial Sequence
<220> FEATURE:
<223> OTHER INFORMATION: Synthesized primer

<400> SEQUENCE: 34
ataatgccga ctgtacttt                                                  19

<210> SEQ ID NO 35
<211> LENGTH: 23
<212> TYPE: DNA
<213> ORGANISM: Artificial Sequence
<220> FEATURE:
<223> OTHER INFORMATION: Synthesized primer

<400> SEQUENCE: 35
ggccttgtag acaccttggt ctt                                             23

<210> SEQ ID NO 36
<211> LENGTH: 21
<212> TYPE: DNA
<213> ORGANISM: Artificial Sequence
<220> FEATURE:
<223> OTHER INFORMATION: Synthesized primer

<400> SEQUENCE: 36
tcactgggga acgaaacagg c                                               21

<210> SEQ ID NO 37
<211> LENGTH: 20
<212> TYPE: DNA
<213> ORGANISM: Artificial Sequence
```

```
<220> FEATURE:
<223> OTHER INFORMATION: Synthesized primer

<400> SEQUENCE: 37
gttcaacaaa cgaaaattgg                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthesized primer

<400> SEQUENCE: 38
ttataaaagc cagtcattag                                                    20

<210> SEQ ID NO 39
<211> LENGTH: 358
<212> TYPE: PRT
<213> ORGANISM: Streptococcus thermophilus

<400> SEQUENCE: 39

Met Ala Asn Lys Thr Lys Ser Lys Ala Leu Leu Glu Lys Met Trp Arg
1               5                   10                  15

Ile Lys Trp Trp Leu Leu Ser Ile Phe Thr Val Leu Phe Leu Leu Phe
                20                  25                  30

Ala Leu Phe Phe Pro Leu Asn Asn Tyr Tyr Val Glu Leu Pro Gly Gly
            35                  40                  45

Ala Phe Asp Thr Lys Glu Val Leu Thr Val Asn Lys Lys Ala Asp Asp
        50                  55                  60

Ser Lys Gly Ser Tyr Asn Phe Val Ala Val Ala Gln Thr Lys Ala Thr
65                  70                  75                  80

Leu Ala Leu Met Leu Tyr Ala Gln Phe Asn Asp Phe Ala Lys Leu Gln
                85                  90                  95

Thr Ala Glu Glu Ala Thr Gly Asn Tyr Ser Asp Glu Asp Phe Met Arg
            100                 105                 110

Ile Asn Gln Phe Tyr Met Glu Thr Ser Gln Asn Gln Ala Val Tyr Gln
        115                 120                 125

Gly Leu Thr Leu Ala Gly Lys Glu Val Ser Leu Glu Tyr Met Gly Val
    130                 135                 140

Tyr Val Leu Gln Val Ala Asp Asp Ser Ser Phe Lys Gly Val Leu Asn
145                 150                 155                 160

Ile Ala Asp Thr Val Thr Ala Val Asn Gly Asn Thr Phe Asp Asn Ser
                165                 170                 175

Thr Asp Met Ile Lys Tyr Val Gln Gly Leu Lys Leu Gly Ser Lys Val
            180                 185                 190

Lys Val Thr Tyr Met Arg Asp Gly Lys Glu Lys Thr Ala Thr Gly Lys
        195                 200                 205

Ile Ile Lys Ile Ala Asn Gly Lys Asn Gly Ile Gly Ile Gly Leu Thr
    210                 215                 220

Asp His Thr Glu Ile Lys Ser Pro Glu Asn Val Lys Phe Lys Leu Asp
225                 230                 235                 240

Gly Val Gly Gly Pro Ser Ala Gly Leu Met Phe Thr Leu Ala Ile Tyr
                245                 250                 255

Asp Gln Val Ser Gly Gln Asp Leu Lys Ala Gly Arg Lys Ile Ala Gly
            260                 265                 270

Thr Gly Thr Ile Glu Lys Asp Gly Ala Val Gly Asp Ile Gly Gly Ala
```

-continued

```
              275             280             285

Tyr Leu Lys Val Lys Ser Ala Ala Asp Ser Gly Ala Asp Ile Phe Phe
    290             295             300

Val Pro Asn Asn Leu Val Thr Lys Glu Met Lys Lys Ala Asp Pro Asp
305             310             315             320

Ala Lys Thr Asn Tyr Gln Glu Ala Lys Glu Ala Ala Glu Lys Leu Gly
            325             330             335

Thr Lys Met Lys Ile Val Pro Val Lys Thr Ala Gln Glu Ala Ile Asp
            340             345             350

Tyr Leu Lys Lys Thr Lys
            355

<210> SEQ ID NO 40
<211> LENGTH: 342
<212> TYPE: PRT
<213> ORGANISM: Streptococcus thermophilus

<400> SEQUENCE: 40

Met Lys Lys Asn Lys Lys Ile Asn Pro Lys Leu Lys Trp Gly Ile Ser
1               5               10              15

Ile Gly Leu Ile Val Val Ala Leu Leu Ala Leu Phe Tyr Pro Thr Ser
            20              25              30

Tyr Tyr Val Glu Met Pro Gly Thr Thr Glu Pro Leu Gly Lys Met Val
            35              40              45

Lys Val Glu Gly Lys Lys Asp Glu His Lys Gly Asp Phe Phe Leu Thr
    50              55              60

Thr Val Gln Ile Ala Arg Ala Asn Leu Ala Thr Met Ile Tyr Ser His
65              70              75              80

Phe Asn Ser Phe Thr Ser Ile Tyr Ser Glu Gln Glu Met Thr Gly Gly
            85              90              95

Leu Asn Asp Ala Gln Phe Asn Arg Val Asn Gln Phe Tyr Met Glu Thr
            100             105             110

Ala Gln Asn Thr Ala Ile Tyr Gln Ala Phe Lys Leu Ala Asn Lys Pro
            115             120             125

Tyr Glu Leu Lys Tyr Glu Gly Val Tyr Val Leu Asp Ile Ala Lys Asn
    130             135             140

Ser Thr Phe Lys Asn Lys Leu Glu Leu Ala Asp Thr Ile Thr Ala Val
145             150             155             160

Asn Gly Gln Gln Phe Thr Ser Ser Ala Asp Met Ile Ala Tyr Val Ser
            165             170             175

Lys Gln Lys Val Gly Asp Ser Val Thr Ile Glu Tyr Thr Arg Ile Asp
            180             185             190

Gly Thr Lys His Lys Ser Thr Gly Lys Tyr Ile Lys Ile Ala Asn Gly
            195             200             205

Lys Thr Gly Ile Gly Ile Ser Leu Val Asp His Thr Glu Val Val Thr
    210             215             220

Thr Pro Lys Val Thr Val Asn Ala Gly Ser Ile Gly Gly Pro Ser Ala
225             230             235             240

Gly Met Met Phe Thr Leu Glu Ile Tyr Ser Gln Leu Thr Gly Lys Asp
            245             250             255

Leu Arg Asn Gly Arg Glu Ile Ala Gly Thr Gly Thr Ile Glu His Asp
            260             265             270

Gly Ser Ile Gly Gln Ile Gly Gly Val Asp Lys Lys Val Ala Thr Ala
    275             280             285
```

```
Ser Lys Glu Gly Ala Lys Val Phe Leu Val Pro Asp Ser Gly Thr Lys
    290                 295                 300

Lys Glu Ser Ser Asn Asn Tyr Leu Gly Ala Lys Thr Ala Ala Lys Lys
305                 310                 315                 320

Leu Lys Thr Lys Met Lys Ile Val Pro Val Lys Thr Ile Gln Asp Ala
            325                 330                 335

Leu Asp Tyr Leu Glu Lys
            340

<210> SEQ ID NO 41
<211> LENGTH: 342
<212> TYPE: PRT
<213> ORGANISM: Streptococcus thermophilus

<400> SEQUENCE: 41

Met Asn Lys Lys Asn Lys Lys Ile Ser Pro Lys Leu Trp Gly Ile Ser
1               5                   10                  15

Ile Gly Leu Ile Ile Val Ala Leu Leu Val Leu Val Tyr Pro Thr Asn
            20                  25                  30

Tyr Tyr Val Glu Met Pro Gly Thr Thr Glu Pro Leu Gly Lys Met Val
        35                  40                  45

Lys Val Glu Gly Lys Lys Asp Glu His Lys Gly Asp Phe Phe Leu Thr
    50                  55                  60

Thr Val Gln Ile Ala Arg Ala Asn Leu Ala Thr Met Ile Tyr Ser His
65                  70                  75                  80

Phe Asn Ser Phe Thr Ser Ile Tyr Ser Glu Gln Glu Met Thr Gly Gly
                85                  90                  95

Leu Asn Asp Ala Gln Phe Asn Arg Val Asn Gln Phe Tyr Met Glu Thr
            100                 105                 110

Ala Gln Asn Thr Ala Val Tyr Gln Ala Phe Lys Leu Ala Asn Lys Pro
            115                 120                 125

Tyr Glu Leu Lys Tyr Glu Gly Val Tyr Val Leu Asp Ile Ala Lys Asn
    130                 135                 140

Ser Thr Phe Lys Asn Lys Leu Glu Leu Ser Asp Thr Ile Thr Ala Val
145                 150                 155                 160

Asn Gly Glu Glu Phe Lys Ser Ser Ala Asp Met Ile Ala Tyr Val Ser
                165                 170                 175

Lys Gln Lys Val Gly Asp Ser Val Thr Ile Glu Tyr Thr Arg Ile Asp
            180                 185                 190

Gly Ser Lys His Lys Ser Thr Gly Lys Tyr Ile Lys Ile Ser Asn Gly
            195                 200                 205

Lys Thr Gly Ile Gly Ile Gly Leu Val Asp His Thr Glu Val Val Thr
    210                 215                 220

Asp Pro Lys Val Thr Val Asn Ala Gly Ser Ile Gly Gly Pro Ser Ala
225                 230                 235                 240

Gly Met Met Phe Thr Leu Glu Ile Tyr Ser Gln Leu Thr Gly Lys Asn
                245                 250                 255

Leu Arg Gly Gly Arg Glu Ile Ala Gly Thr Gly Thr Ile Glu His Asp
            260                 265                 270

Gly Ser Ile Gly Gln Ile Gly Gly Val Asp Lys Lys Val Ala Thr Ala
            275                 280                 285

Ser Lys Glu Gly Ala Lys Val Phe Leu Val Pro Asp Ser Gly Thr Lys
    290                 295                 300

Lys Glu Ser Ser Asn Asn Tyr Leu Gly Ala Lys Ala Ala Ala Lys Lys
305                 310                 315                 320
```

-continued

```
Leu Lys Thr Lys Met Lys Ile Val Pro Val Lys Thr Ile Gln Asp Ala
            325                 330                 335

Leu Thr Tyr Leu Glu Lys
            340

<210> SEQ ID NO 42
<211> LENGTH: 186
<212> TYPE: PRT
<213> ORGANISM: Streptococcus thermophilus

<400> SEQUENCE: 42

Met Lys Lys Ile Asn Leu Ala Leu Leu Thr Leu Ala Thr Leu Met Gly
1               5                   10                  15

Val Ser Ser Thr Ala Val Val Phe Ala Asp Asp Ala Ser Gln Tyr Ser
            20                  25                  30

Arg Glu Asp Asn Asn Cys Thr His Phe Pro Val Gly Gln Ser His Met
        35                  40                  45

Leu Leu Glu Leu Arg Thr Ala Phe Ser Gln Val Lys Thr Phe Phe Gln
    50                  55                  60

Thr Lys Asp Gln Leu Asp Asn Ile Leu Leu Thr Asp Ser Leu Met Gln
65                  70                  75                  80

Asp Phe Lys Gly Tyr Leu Gly Cys Gln Ala Leu Ser Glu Met Ile Gln
                85                  90                  95

Phe Tyr Leu Val Glu Val Met Pro Gln Ala Glu Lys His Gly Pro Glu
            100                 105                 110

Ile Lys Glu His Leu Asn Ser Leu Gly Glu Lys Leu Lys Thr Leu Arg
        115                 120                 125

Met Arg Leu Arg Arg Cys His Arg Phe Leu Pro Cys Glu Asn Lys Ser
    130                 135                 140

Lys Ala Val Glu Gln Val Lys Ser Asp Phe Asn Lys Leu Gln Asp Gln
145                 150                 155                 160

Gly Val Tyr Lys Ala Met Asn Glu Phe Asp Ile Phe Ile Asn Cys Ile
                165                 170                 175

Glu Ala Tyr Met Met Ile Lys Ile Lys Ser
            180                 185

<210> SEQ ID NO 43
<211> LENGTH: 97
<212> TYPE: PRT
<213> ORGANISM: Streptococcus thermophilus

<400> SEQUENCE: 43

Ser Ala Ala Val Thr Gly Val Pro Val Lys Gly Gln Asp Thr Val Lys
1               5                   10                  15

Gly Arg Val Pro Phe Asn Gly Gln Asp Pro Val Lys Gly Gln Val Ser
            20                  25                  30

Val Lys Gly Gln Asp Lys Val Lys Ala Gln Glu Pro Val Lys Gly Pro
        35                  40                  45

Val Ser Thr Lys Pro Gly Ser Cys Pro Ile Ile Leu Ile Arg Cys Ala
    50                  55                  60

Met Leu Asn Pro Pro Asn Arg Cys Leu Lys Asp Thr Asp Cys Pro Gly
65                  70                  75                  80

Ile Lys Lys Cys Cys Glu Gly Ser Cys Gly Met Ala Cys Phe Val Pro
                85                  90                  95

Gln
```

1

GRAM-POSITIVE BACTERIA OF THE SPECIES *LACTOCOCCUS LACTIS* OR *STREPTOCOCCUS THERMOPHILUS* HAVING A VERY LOW SURFACE PROTEOLYSIS, PROCESSES FOR OBTAINING THEM AND USES THEREOF

CROSS-REFERENCES TO RELATED APPLICATIONS

This application is a National Stage of International Application No. PCT/EP2021/055561 filed Mar. 5, 2021, which claims priority to French Patent Application No. 2002268, filed Mar. 6, 2020, the entire disclosures of which are hereby incorporated by reference.

STATEMENT REGARDING SEQUENCE LISTING

The sequence listing associated with this application is provided in text format in lieu of a paper copy and is hereby incorporated by reference into the specification. The name of the text file containing the sequence listing is 2095-P355US.PNP Seq List 20251121 ST25.txt. The text file is 88 KB; was created on Nov. 21, 2025; and is being submitted via Patent Center w with the filing of the specification.

The present invention relates to Gram-positive bacteria of the species *Lactococcus lactis* or *Streptococcus thermophilus* having very low surface proteolysis; it also relates to the use of these bacteria, particularly for the production of proteins of interest.

An analysis of peptides produced by the bacterium *Lactococcus lactis* and accumulated in its culture medium revealed a high accumulation of peptides of bacterial origin (Guillot et al., 2016). This set of peptides defines the exocellular peptidome or exopeptidome of the bacterium. Analysis of these peptides shows that approximately half of them originate from the degradation of surface proteins that are neither cytoplasmic nor transmembrane.

This degradation would be due to the presence of several proteases localized on the surface of the bacteria. Two such localized proteases have already been characterized in lactic bacteria. One, a serine protease of the subtilisin family, called PrtS in *Streptococcus thermophilus* (*S. thermophilus*) and PrtP in *Lactococcus lactis* (*L. lactis*), is covalently anchored to the wall and is able to hydrolyze milk caseins (Fernandez-Espla et al., 2000 and Siezen et al., 1999). The second, also a serine protease, called HtrA, has been characterized in *L. lactis* (Poquet et al., 2000); a homologue in *S. thermophilus* is also present. This protease hydrolyzes abnormal and/or misfolded proteins and is involved in the maturation of exported proteins (Poquet et al., 2000).

One of the main drawbacks of this surface proteolysis is encountered during the production of proteins of interest by bacteria, especially Gram-positive bacteria. Indeed, surface proteolysis leads to a degradation of these proteins during and/or after their export, leading to a decrease in yield and/or an alteration of the structure and activity of the protein of interest.

It therefore appears desirable to obtain bacterial strains with very low surface proteolysis compared to wild type strains.

In this context, the Inventors constructed single and double mutants for PrtS and HtrA in *S. thermophilus* strain LMD9 (see Example 1) and came to the conclusion that deletion of both PrtS and HtrA proteases does not abolish surface proteolysis in *S. thermophilus* LMD9 since residual proteolysis is observed (see Example 2). The same results were obtained for *L. lactis* strains MG1363 and IL1403 (Guillot et al., 2016) and thus confirm that the surface proteases HtrA and PrtS/PrtP alone are not responsible for all of the surface proteolytic activity in these strains. Hafeez et al. (2013 and 2015) created a ΔprtS-ΔhtrA double mutant in *S. thermophilus* and concluded that exopeptidases with carboxypeptidase, peptidyl peptidase, aminopeptidase, and X-prolyl-dipeptidyl peptidase activities may be present, the possible presence of such exopeptidases, however, does not explain the residual protease activity observed by the Inventors, as the enzymes are of different nature. Indeed, exopeptidases act on the ends of peptide chains, whereas the residual proteolysis observed results from internal protein cleavages.

The Inventors hypothesized that one or more proteases responsible for this residual activity are present in each of the three strains. Thus, they identified the protease Ster-1612 (or STER_RS07910 in the new NCBI annotation) in the wild-type strain LMD9 of *S. thermophilus*; this protease is named YwdF (or EFV54_RS11495 in the new NCBI annotation) for strain IL1403 of *L. lactis* subsp. *lactis* and llmg-2442 (or LLMG_RS12255 in the new NCBI annotation) for *L. lactis* subsp. *cremoris* strain MG1363 (see Example 3). This protease belongs to the S16 family of LonA proteases (Gottesman et al., 1978 and Charrette et al., 1981) which are serine proteases, characterized by the presence of a conserved Serine—Lysine catalytic dyad in the C-terminal region of the protein (Botos et al., 2004).

The Inventors then constructed strains derived from *S. thermophilus* LMD9 in which all or part of the three endogenous proteases PrtS, HtrA and Ster-1612 were inactivated (see Example 1); inactivation of the three proteases leads to nearly abolished surface proteolysis in this bacterium (see Example 4). In addition, they constructed the *S. thermophilus* LMD9 strain in which the three proteases PrtS, HtrA and Ster-1612 were inactivated and producing the heterologous proteins IL-10 or elafin (see example 6) and confirmed that the inhibition of these three proteases did not lead to any further degradation of heterologous proteins, thus allowing the improvement of the yield of heterologous protein production, compared to the wild type parent bacterium (see example 7). These results were also observed in *Lactococcus lactis* (see Example 11).

The object of the present invention is therefore a Gram-positive bacterium of the species *Lactococcus lactis* or *Streptococcus thermophilus*, such that the endogenous surface protease homologous to the protein designated Ster-1612 in *Streptococcus thermophilus* LMD9 and Ywdf or llmq 2442 in *Lactococcus lactis* IL1403 and MG1363, respectively, has a decreased or abolished expression and/or activity; more particularly, it relates to a Gram-positive bacterium of the species *Lactococcus lactis* or *Streptococcus thermophilus*, such that the endogenous surface protease comprising an amino acid motif having at least 80% identity with the sequence SEQ ID No. 1, has a decreased or abolished expression and/or activity, wherein SEQ ID No. 1 is defined as follows:

I-A-G-T-G-T-I-E-X1-D-G-X2-X3-G-X4-I-G-G-X5-X6-X7-K with

X1 is histidine (H) or lysine (K);
X2 is serine (S), alanine (A) or threonine (T);
X3 is isoleucine (I), leucine (L) or valine (V);
X4 is aspartic acid (D) or glutamine (Q);

X5 is alanine (A) or valine (V);

X6 is aspartic acid (D) or tyrosine (Y);

and X7 is lysine (K) or leucine (L).

The endogenous surface protease is a serine protease whose enzymatic activity can be characterized by the evaluation of the degradation of a chromogenic substrate by colorimetric assay, or of a protein substrate by SDS-PAGE electrophoresis or by HPLC analysis.

Preferably, the amino acid motif comprised in said protease has at least 80% identity, and in ascending order of preference at least 82%, 86%, 91%, 95% or 100% identity with the amino acid sequence SEQ ID No. 1 when the sequences are aligned along their entire length.

According to a particular embodiment, the Gram-positive bacterium is of the species *Streptococcus thermophilus* and the endogenous surface protease has at least 70% identity, and in order of increasing preference at least 75%, 80%, 85%, 90%, 91%, 92%, 93%, 94%, 95%, 96%, 97%, 98%, 99% or 100%, and particularly preferably at least 90% identity with the sequence SEQ ID No. 2 when the sequences are aligned along their entire length. In particular, the endogenous surface protease is Ster-1612 of sequence SEQ ID No 2.

According to yet another embodiment, the Gram-positive bacterium is of the species *Lactococcus lactis* and the endogenous surface protease has at least 70% identity, and in increasing order of preference at least 75%, 80%, 85%, 90%, 91%, 92%, 93%, 94%, 95%, 96%, 97%, 98%, 99% or 100%, and particularly preferably at least 80% identity with the sequence SEQ ID No. 3 or with the sequence SEQ ID No. 4 when the sequences are aligned over their entire length. In particular, the Gram-positive bacterium can be *Lactococcus lactis* subsp. *lactis* and the endogenous surface protease is YwdF of sequence SEQ ID No. 3 or the Gram-positive bacterium can be *Lactococcus lactis* subsp. *cremoris* and the endogenous surface protease is llmg 2442 of sequence SEQ ID No. 4.

Unless otherwise specified, percent identities are calculated from a global alignment of amino acid sequences performed using the "needle" algorithm (Needleman and Wunsch, 1970) using the default parameters "Matrix": EBLOSUM62, "Gap penalty": 10.0 and "Extend penalty": 0.5.

The nucleotide sequence of the gene encoding Ster-1612 is represented by the sequence SEQ ID No. 5. The nucleotide sequence of the gene coding YwdF is represented by the sequence SEQ ID No. 6. The nucleotide sequence of the gene coding llmg_2442 is represented by the sequence SEQ ID No. 7.

The analysis of 102 genomes of the subspecies *L. lactis* subsp. *lactis*, allowed to define a degree of conservation of YwdF higher than 80% for 100 strains, the last 2 apparently not having the gene coding YwdF. Sequence conservation is also high within the *L. lactis* subsp. *cremoris* subspecies, since among the 56 genomes analyzed, 51 have a gene encoding a protein that is more than 80% identical to the llmg_2442 protein of *L. lactis* subsp. *cremoris* MG1363, while 5 do not seem to have the gene encoding this protein.

By way of illustration and without limitation, the Gram-positive bacterium according to the invention can be obtained from a strain of *S. thermophilus* LMD9, *S. thermophilus* CNRZ1066, *Lactococcus lactis* subsp. *lactis* IL1403, *Lactococcus lactis* subsp. *cremoris* MG1363.

The bacterium according to the invention shows a significantly decreased surface proteolysis compared to the parent bacterium from which it is derived (see the protocol for quantifying proteolysis in Example 2).

By "the expression of an endogenous surface protease in a bacterium is decreased" is meant the decrease in the quantity of the protease produced by the bacterium of the invention in comparison with the parent bacterium from which it is derived and in which the expression of said protease is not decreased, whatever the cause (decrease in the level of expression of the gene coding for the protease, reduction in the number of messenger RNAs, degradation of the protease).

Methods used to measure the decrease in expression of a protease in a bacterium include, for example, quantitative RT PCR to assess the expression level of the gene encoding the protease or protein assay by Elisa to quantify the protein synthesized.

By "the activity of an endogenous surface protease in a bacterium is decreased" is meant the decrease in the activity of the protease produced by the bacterium according to the invention in comparison with a parent bacterium from which it is derived and in which the activity of said protease is not decreased.

Methods used to measure the decrease in protease activity in a bacterium include, for example, counting surface peptides identified by mass spectrometry following chromatographic double separation (Guillot et al., 2016), assessing the degradation of a chromogenic substrate that allows easy quantification of activity by colorimetric assay, or of a protein substrate by SDS-PAGE electrophoresis or HPLC liquid chromatography analysis . . . .

By "the expression and/or activity of an endogenous surface protease in a bacterium is abolished" is meant the absence of expression and/or activity of the protease or even the absence of expression and/or activity of at least one of the other known proteases (HtrA and/or PrtS in *Streptococcus thermophilus*, HtrA and/or PrtP in *Lactococcus lactis*, as described below); this is the case when the proteolysis of the bacterium in question represents, in order of preference, less than 60%, 50%, 40%, 30%, even more preferably less than 10%, and most preferably less than 5% of the proteolysis of the parent bacterium from which it is derived, according to the protocol for quantifying proteolysis in Example 2. Such an abolition of the expression and/or activity of the endogenous surface protease can be obtained by a total decrease of the expression and/or activity of the protease (in the sense defined below) or can occur when the structural gene of the protease is not naturally present in the genome of the bacterium, or present in a truncated form (pseudogene).

According to a particular embodiment, the bacterium according to the invention having a decreased activity and/or expression of its endogenous surface protease further has a decreased activity and/or expression of at least one other endogenous surface protease which may be HtrA and/or PrtS in *Streptococcus thermophilus*, HtrA and/or PrtP in *Lactococcus lactis*.

Preferably, the bacterium of the species *S. thermophilus* according to the invention is further such that the endogenous surface protease having at least 70% identity with the sequence SEQ ID No. 8 (HtrA) or the endogenous surface protease having at least 70% identity with the sequence SEQ ID No. 9 (PrtS) has a decreased or abolished expression and/or activity.

Preferably, the bacterium of the species *L. lactis* according to the invention is further such that the endogenous surface protease having at least 70% identity with the sequence SEQ ID No. 10 (HtrA) or the endogenous surface protease having at least 70% identity with the sequence SEQ ID No. 11 (PrtP) has a decreased or abolished expression and/or activity.

The surface protease, designated HtrA in *Streptococcus thermophilus*, has at least 70% identity, and in order of preference at least 75%, 80%, 85%, 90%, 91%, 92%, 93%, 94%, 95%, 96%, 97%, 98%, 99% or 100% identity with the amino acid sequence SEQ ID No. 8, when the sequences are aligned along their entire length. The surface protease, designated HtrA in *Lactococcus lactis*, has at least 70% identity, and in increasing order of preference at least 75%, 80%, 85%, 90%, 91%, 92%, 93%, 94%, 95%, 96%, 97%, 98%, 99% or 100% identity with the amino acid sequence SEQ ID No. 10, when the sequences are aligned over their entire length.

The nucleotide sequence of the gene encoding HtrA is represented by the sequence SEQ ID No. 12 in the case of a strain of *S. thermophilus*, and by the sequence SEQ ID No. 13 in the case of a strain of *Lactococcus lactis*.

The surface protease, designated PrtS in *Streptococcus thermophilus*, has at least 70% identity, and in increasing order of preference at least 75%, 80%, 85%, 90%, 91%, 92%, 93%, 94%, 95%, 96%, 97%, 98%, 99%, or 100% identity with the amino acid sequence SEQ ID No. 9, when the sequences are aligned along their entire length. The surface protease, designated PrtP in *Lactococcus lactis*, has at least 70% identity, and in increasing order of preference at least 75%, 80%, 85%, 90%, 91%, 92%, 93%, 94%, 95%, 96%, 97%, 98%, 99% or 100% identity with the amino acid sequence SEQ ID No. 11, when the sequences are aligned over their entire length.

The nucleotide sequence of the gene encoding PrtS is represented by the sequence SEQ ID NO. 14 in the case of a strain of *S. thermophilus*, by the sequence SEQ ID NO. 15 in the case of a strain of *Lactococcus lactis*.

According to another embodiment of the invention, the bacterium of the species *S. thermophilus* according to the invention is such that the endogenous surface protease having at least 70% identity with the sequence SEQ ID No. 8 (HtrA) and the endogenous surface protease having at least 70% identity with the sequence SEQ ID No. 9 (PrtS) have a decreased or abolished expression and/or activity.

According to another embodiment of the invention, the bacterium of the species *L. lactis* according to the invention is such that the endogenous surface protease having at least 70% identity with the sequence SEQ ID No. 10 (HtrA) and the endogenous surface protease having at least 70% identity with the sequence SEQ ID No. 11 (PrtP) have a decreased or abolished expression and/or activity.

In the present case, the decrease in the expression of each of the three endogenous surface proteases in a bacterium according to the invention is measured, for example, by quantitative RT PCR to assess the level of expression of each of the genes encoding the proteases, or by ELISA assay to quantify each of the proteins synthesized, and is compared to the expression of the surface proteases of a parent bacterium from which it is derived.

The decrease in the overall activity of the three endogenous surface proteases in a bacterium according to the invention can be measured by counting the surface peptides identified by mass spectrometry following a double liquid chromatography separation (HPLC) and is compared to the overall activity of the surface proteases of a parent bacterium from which it is derived.

The decrease in expression and/or activity of the proteases can be total or partial. The decrease in expression and/or activity is considered total in the sense of the invention when it represents less than 5% of the proteolysis of the parent bacterium from which it is derived, according to the protocol for quantifying proteolysis in Example 2 and as observed with bacteria not expressing any of the three endogenous surface proteases (see Example 4). It is considered partial when it is significantly lower than that of the parent bacterium from which it is derived. The significance of the difference is estimated by a statistical test adapted to small sample sizes (non-parametric Kruskal-Wallis test) with a probability P less than 0.05. The significant decrease in this surface proteolysis observed for a bacterium according to the invention leads to a proteolysis, in order of preference, of less than 60%, 50%, 40%, 30% still preferably less than 10%, compared to the surface proteolysis of the parent bacterium from which it is derived. A partial decrease in protease expression and/or activity is observed with bacteria that do not express one or two of the three endogenous surface proteases mentioned above (see Examples 2 and 4).

Decreasing the expression and/or activity of endogenous surface proteases as defined above in a bacterium, can be achieved in different ways detailed below.

This decrease in the expression and/or activity of endogenous surface proteases can be obtained by mutagenesis of the genes encoding these proteases. This mutagenesis can then occur at the level of the coding sequence or the sequences regulating the expression of these genes, in particular at the level of the promoter, leading to an inhibition of the transcription or translation of the proteases. For example, the introduction of one or more point mutations within the coding sequence of a gene or its expression regulation sequences can induce, depending on the nature of the mutation a shift of the reading frame and/or the introduction of a stop codon in the sequence and/or the inhibition of the transcription or translation of the genes encoding these 3 proteases and/or a substitution of one of the amino acids of the active site of the enzyme and lead to the expression of an inactive protease, or a protease with a decreased activity. Finally, when the gene encoding one of the surface proteases is organized in an operon (case of ster-1612 in *S. thermophilus*, and probably of YwdF and llmg2442 in *L. lactis*), the introduction of one or more point mutations within the coding sequence of a gene of the operon other than the one coding the protease can induce, depending on the nature of the mutation, a shift of the reading frame and/or the introduction of a stop codon in the sequence and thus abolish the expression of the protease (polar mutation). The same is true for the sequence regulating the expression of the whole operon.

The bacterium according to the invention can be obtained by deletion, insertion and/or substitution of one or more nucleotides, for example by deletion of all or part of the coding sequence of the gene encoding the protease or of its promoter, by insertion of an exogenous sequence within the coding sequence of the gene encoding the protease or of its promoter by the substitution of one or more nucleotides of the coding sequence of the gene encoding one of the amino acids of the active site of the protease or of its promoter, or by introduction of a polar mutation in the case of a gene organized in an operon. Methods for deleting, inserting and/or substituting a given genetic sequence in bacteria, in particular in *S. thermophilus* and *Lactococcus lactis*, are well known to the skilled person (Gardan et al., 2009 and Biswas et al., 1993). For example, the insertion of an exogenous sequence within the coding sequence of the gene encoding the protease can be achieved by using transposons of natural or artificial origin.

Mutagenesis can be implemented by inducing random mutations, for example using physical agents, such as radiation or chemical agents such as EMS (Ethyl Methane Sulfonate) or in a targeted manner by transfection, transduction, natural transformation or electroporation (Bron et al., 2019). Alternatively, mutagenesis can be implemented by methods using nucleases (TALEN, CRISPR/Cas9, Wei et al., 2013).

The decrease of protease activity can be achieved by the use of specific serine protease inhibitors (PMSF [Phenyl-MethaneSulfonyl Fluoride], DFP [DiisopropylFluoroPhosphate], triterpenoid, coumarin, serpins, peptidomimetics . . . , Shamsi et al., 2016; Soualmia and El Amri, 2018). Finally, the decrease in protease expression can be achieved by modification of the promoter sequence of the gene according to for example one of the methods used to substitute a nucleotide sequence cited above, or by an RNA interference (RNAi) technique, by expression of an antisense RNA or by aptamers.

The mutated genes encoding the proteases as defined above can be identified, for example, by PCR using primers specific to said genes, PCR possibly followed by sequencing of the PCR fragment in the case of mutations not affecting the size of said gene (substitutions, for example).

The Inventors searched for the presence of the genes encoding these three surface proteases, STER_1612, HtrA and PrtS, in 61 S. thermophilus genomes, and the conservation of the corresponding protein sequences was analyzed. The variability in the presence of the PrtS protease within the S. thermophilus species was already known (Delorme et al., 2010). In contrast, the two proteases HtrA and STER_1612 are present in all strains, and their protein sequences are very well conserved (except for one strain, N4L, whose gene encoding HtrA is thought to be a pseudogene).

Thus, two groups of S. thermophilus strains can be distinguished on the basis of their surface protease equipment: a group A of 24 strains that possess the three proteases PrtS, HtrA and STER_1612, to which the strain LMD9 belongs, and a group B of 37 strains that possesses the two proteases HtrA and STER_1612 and does not possess the protease PrtS, to which the strain CNRZ1066 belongs.

The Inventors evaluated the role of the two surface proteases HtrA and STER_1612 on the surface proteolysis of group B S. thermophilus strains and showed that the residual surface proteolysis of the double mutant is comparable to that obtained with the triple mutant of the LMD9 strain (see Example 5).

Whether the S. thermophilus strain has two or three surface proteases, inactivation of the genes coding for these two or three surface proteases respectively is sufficient to reduce the surface proteolysis of the bacteria by more than 90%.

An advantageous bacterium within the meaning of the present invention is a bacterium, preferably Streptococcus thermophilus, in which the expression or activity of the 3 endogenous surface proteases, Ster-1612 of sequence SEQ ID No. 2, HtrA of sequence SEQ ID No. 8, and PrtS of sequence SEQ ID No. 9, of said bacterium is inhibited.

Another advantageous bacterium in the sense of the present invention is a bacterium, preferably Streptococcus thermophilus, in particular a strain of Streptococcus thermophilus which would not possess PrtS, in which the expression or activity of the endogenous surface protease, Ster-1612 of sequence SEQ ID No. 2 or in which the expression or activity of the 2 endogenous surface proteases, Ster-1612 of sequence SEQ ID No. 2 and HtrA of sequence SEQ ID No. 8 of said bacterium is inhibited.

Similarly, some strains of L. lactis do not naturally express the PrtP protease. Again, the Inventors were able to show that such strains modified to have both endogenous surface proteases YwdF or llmg2442 (or their homologues) and HtrA with reduced activity or expression exhibit very low surface proteolysis (see Example 9).

An advantageous bacterium within the meaning of the present invention is a bacterium, preferably Lactococcus lactis, in which the expression or activity of the 3 endogenous surface proteases, YwdF or llmg2442 (or their homologues) of respective sequence SEQ ID No. 3 or 4, HtrA of sequence SEQ ID No. 10, and PrtP of sequence SEQ ID No. 11, of said bacterium is inhibited.

Another advantageous bacterium in the sense of the present invention is a bacterium, preferably Lactococcus lactis, in particular a strain of Lactococcus lactis which would not possess PrtP, in which the expression or activity of the endogenous surface protease, YwdF or llmg2442 (or their homologues) of respective sequence SEQ ID No. 3 or 4 or in which the expression or activity of the 2 endogenous surface proteases, and YwdF or llmg2442 of respective sequence SEQ ID No. 3 or 4 and HtrA of sequence SEQ ID No. 10 of said bacterium is inhibited.

Thus the present invention relates to:
bacteria not expressing the endogenous surface protease defined by its identity with SEQ. ID. No. 1; i.e., Ster-1612 (or its homolog) in Streptococcus thermophilus and Ywdf or llmq 2442 (or its homolog) in Lactococcus lactis;
bacteria not expressing two endogenous surface proteases: Ster-1612 (or its homolog) and HtrA in Streptococcus thermophilus; Ster-1612 (or its homolog) and PrtS in Streptococcus thermophilus; Ywdf or llmq 2442 (or its homolog) and HtrA in Lactococcus lactis; and Ywdf or llmq 2442 (or its homolog) and PrtP in Lactococcus lactis; and
bacteria not expressing three endogenous surface proteases: Ster-1612 (or its homolog), HtrA and PrtS in Streptococcus thermophilus; and Ywdf or llmq 2442 (or its homolog), HtrA and PrtP in Lactococcus lactis.

Another object of the present invention is a bacterium as defined above, modified to express a protein of interest, for example a heterologous or recombinant protein of interest, said bacterium being transformed by an expression vector containing a DNA fragment coding for the protein of interest, or by integrating the DNA fragment of interest into the chromosome of said bacterium.

Heterologous protein means a protein that is neither naturally produced by the bacterial strain nor necessary for its growth.

The advantage of the present invention is therefore the expression by the bacterium according to the present invention of proteins of industrial interest, which will be secreted into the culture medium of said bacterium and in which the proteins of interest can be easily recovered, or associated with the bacterial surface and exerting their enzymatic activity on the external surface of the bacterium. By bacterial surface-associated protein is meant a protein covalently anchored to the bacterial wall via a specific sortase anchoring motif, a protein inserted into the plasma membrane via a membrane anchor located at the N- or C-terminal end of its amino sequence, a protein covalently bound to the membrane via a lipid anchor motif located at the N-terminus of its amino sequence or a protein with non-covalent association motifs to the wall such as LysM (Cossart and Joncquières, 2000; Desvaux et al., 2018).

Another object of the present invention is a process for the preparation of a Gram-positive bacterium of the species Lactococcus lactis or Streptococcus thermophilus with low proteolytic activity, comprising the reduction or abolition in said bacterium of the expression and/or activity of an endogenous surface protease of said bacterium, said protease comprising an amino acid motif having at least 80%, and preferably in ascending order at least 82%, 86%, 91%, 95% or 100% identity with the sequence SEQ ID No. 1,
    wherein SEQ ID No. 1 is defined as follows:

I-A-G-T-G-T-I-E-X1-D-G-X2-X3-G-X4-I-G-G-X5-X6-X7-K with
    X1 is histidine (H) or lysine (K);
    X2 is serine (S), alanine (A) or threonine (T);
    X3 is isoleucine (I), leucine (L) or valine (V);
    X4 is aspartic acid (D) or glutamine (Q);
    X5 is alanine (A) or valine (V);
    X6 is aspartic acid (D) or tyrosine (Y);
    and X7 is lysine (K) or leucine (L).

Preferably, the endogenous surface protease in *Streptococcus thermophilus* has at least 70% and even more preferably 90% identity with the sequence SEQ ID No. 2 and the endogenous surface protease in *Lactococcus lactis* has at least 70% and even more preferably 80% identity with the sequence SEQ ID No. 3 or with the sequence SEQ ID No. 4

Preferably, the process for preparing a low proteolytic *Streptococcus thermophilus* bacterium according to the invention further comprises decreasing or abolishing in said bacterium the expression and/or activity of the endogenous surface protease having at least 70% identity with the sequence SEQ ID No. 8 (HtrA) and/or the endogenous surface protease having at least 70% identity with the sequence SEQ ID No. 9 (PrtS).

Preferably, the process for preparing a low proteolytic *Lactococcus lactis* bacterium according to the invention further comprises decreasing or abolishing in said bacterium the expression and/or activity of the endogenous surface protease having at least 70% identity with the sequence SEQ ID No. 10 (HtrA) and/or of the endogenous surface protease having at least 70% identity with the sequence SEQ ID No. 11 (PrtP).

By "low proteolytic bacterium" is meant a bacterium with a very low surface proteolysis compared to the parent bacterium from which it is derived, i.e. estimated at less than 10% and preferably less than 5% of the proteolysis of the parent bacterium from which it is derived.

Decreasing the expression and/or activity of these proteases can be achieved as described above.

Another object of the present invention is a method for decreasing or abolishing the proteolytic activity of proteases in a Gram-positive bacterium of the species *Lactococcus lactis* or *Streptococcus thermophilus*, comprising decreasing or abolishing in said bacterium of the expression and/or activity of an endogenous surface protease of said bacterium, said protease comprising an amino acid motif having at least 80%, and preferably in ascending order at least 82%, 86%, 91%, 95% or 100% identity with the sequence SEQ ID No. 1,
    wherein SEQ ID No. 1 is defined as follows:

I-A-G-T-G-T-I-E-X1-D-G-X2-X3-G-X4-I-G-G-X5-X6-X7-K with
    X1 is histidine (H) or lysine (K);
    X2 is serine (S), alanine (A) or threonine (T);
    X3 is isoleucine (I), leucine (L) or valine (V);
    X4 is aspartic acid (D) or glutamine (Q);

X5 is alanine (A) or valine (V);
    X6 is aspartic acid (D) or tyrosine (Y);
    and X7 is lysine (K) or leucine (L).

Preferably, the endogenous surface protease in *Streptococcus thermophilus* has at least 70% and more preferably 90% identity with the sequence SEQ ID No. 2 and the endogenous surface protease in *Lactococcus lactis* has at least 70% and more preferably 80% identity with the sequence SEQ ID No. 3 or with the sequence SEQ ID No. 4

Preferably, the method for decreasing or abolishing the proteolytic activity of proteases in a *Streptococcus thermophilus* bacterium further comprises decreasing or abolishing in said bacterium the expression and/or activity of the endogenous surface protease having at least 70% identity with the sequence SEQ ID No. 8 (HtrA) and/or the endogenous surface protease having at least 70% identity with the sequence SEQ ID No. 9 (PrtS).

Preferably, the method for decreasing or abolishing the proteolytic activity of proteases in a *Lactococcus lactis* bacterium further comprises decreasing or abolishing in said bacterium the expression and/or activity of the endogenous surface protease having at least 70% identity with the sequence SEQ ID No. 10 (HtrA) and/or of the endogenous surface protease having at least 70% identity with the sequence SEQ ID No. 11 (PrtP)

Another object of the present invention is the use of a bacterium according to the present invention for the production of heterologous protein of interest, said bacterium being transformed by an expression vector containing a DNA fragment coding for the heterologous protein of interest or by integration of the DNA fragment of interest into the chromosome of said bacterium.

Among the heterologous proteins of interest is elafin, which is an inhibitor of proteolytic activity. This activity is particularly sought after, especially for the treatment of chronic inflammatory bowel diseases, in which the activity of human proteases must be inhibited (Bermudez-Humaran et al., 2015). More generally, we can mention anti-inflammatory proteins targeting the mucosal immune system (cytokines, human trefoil factor TFF-1 . . . ), vaccine proteins (fragment C of tetanus toxin, E7 antigen of human papillomavirus,), antibacterial peptides targeting imbalances in the intestinal flora (defensins, cathelidicins, PAP protein associated with pancreatitis), enzymes palliating deficiencies or deficiencies (superoxide dismutase, phenylalanine hydroxylase, glutamate decarboxylase), etc (Neirynck and Steidler, 2006; Bermudez-Humaran et al., 2013, Bermudez-Humaran and Langella, 2018). Proteins of interest in animal health (antiviral vaccine proteins, for example) or proteins of technological interest (esterase, aminotransferase . . . ) can also be considered.

Among the bacterial strains used for the production of heterologous proteins of interest are *L. lactis* and *S. thermophilus* strains.

*Lactococcus lactis* is considered as the reference bacterium for the production of molecules of therapeutic interest. Its use has several advantages: it is a food bacterium whose safety is recognized (GRAS and QPS labelled bacterium), it can be genetically manipulated and a deletion mutant of the gene coding for the HtrA protease is available. It was then shown that the production of elafin by this mutant was higher than that of the wild-type strain, and that the treatment of mice with colitis by oral administration of the mutated strain was more effective than with the wild-type strain (Bermudez-Humaran et al., 2015).

Moreover, *Streptococcus thermophilus* according to the invention also has many advantages: it is thermophilic, its temperature optimum corresponds to the temperature of the human body of 37° C., it is easily transformable and totally devoid of surface proteolytic activity, which avoids the degradation of the heterologous protein of interest as it is produced.

A particularly advantageous bacterium for the production of heterologous proteins of interest is an *S. thermophilus* bacterium as defined herein.

Another object of the present invention is a process for producing a heterologous protein, using a bacterium of the invention, as defined above.

It is also an object of the present invention to use a bacterium according to the present invention as a pre-maturation ferment for milk.

One of the problems in dairy technology is the variation in the composition of non-protein nitrogen (free amino acids and peptides) in milk. This is particularly pronounced when animals change their diet, resulting in summer and winter milks with very different compositions. These variations in non-protein nitrogen composition are at the origin of varia-tions in the growth of lactic acid bacteria in milk, this growth being closely dependent on the use of these non-protein nitrogen sources. These growth variations lead to a lack of reproducibility of fermentation times, which is a difficulty for the dairy industry.

The use of a bacterium according to the present invention as a pre-maturation ferment of the milk allows to abolish these variations. Indeed, in the first step, which corresponds to the pre-maturation step, the usable non-protein nitrogen sources would be consumed, without surface proteases being able to hydrolyze the milk proteins and generate new non-protein nitrogen sources. In a second step, the growth of the sourdough used to ferment the milk would only rely on its ability to hydrolyze the caseins, which is carried by the PrtP and PrtS proteases, depending on the bacteria consid-ered. Such an operation therefore has the effect of standard-izing the growth of the sourdough, by abolishing the varia-tions in growth due to variations in the composition of the milk in non-protein nitrogen.

A particularly advantageous bacterium as a milk pre-maturation ferment is a strain of *S. thermophilus* as defined herein.

The present invention will be better understood with the aid of the following description, which refers to the non-limiting examples illustrating the very low surface prote-olytic activity of a bacterium according to the invention in which the 2 (strain CNRZ1066ΔhtrAΔster_1612) or 3 (strain LMD9ΔhtrAΔprtSΔster_1612) proteases as defined in the invention are inhibited compared to the parent bac-terial strain from which it is derived (strain CNRZ1066 or strain LMD9), as well as the appended figures:

FIG. 1: Effect of inactivation of the two surface proteases PrtS and HtrA on the presence of peptides from the degra-dation of *S. thermophilus* LMD9 surface proteins in the culture medium. Mean of 3 experiments (black), with stan-dard deviation of the mean (gray).

FIG. 2: Sequence alignment of the three proteins STER_1612 (SEQ ID NO: 39), YwdF (SEQ ID NO: 40) and llmg_2442 (SEQ ID NO: 41). The multiple alignment was performed with MUSCLE (v3.8) available on the EMBL-EBI server (www.ebi.ac.uk). White characters on black background indicate amino acids located inside the cell, italic characters correspond to the transmembrane fragment and black ones are located outside the cell (HMMTOP predictions). Amino acids potentially constituting the cata-lytic diad are highlighted in gray.

FIG. 3: Growth of *S. thermophilus* LMD9 wild type strain and mutated strain for the three surface proteases PrtS, HtrA and STER_1612 (triple mutant) in chemically defined medium (CDM) containing only free amino acids as a source of amino nitrogen.

FIG. 4: Effect of inactivation of the 3 surface proteases PrtS, HtrA, and STER_1612 on the number of peptides from *S. thermophilus* LMD9 surface protein degradation. Average of 3 experiments (black), with standard deviation of the mean (gray).

FIG. 5: Coverage of IL-10 (SEQ ID NO: 42) and elafin (SEQ ID NO: 43) proteins by the degradation fragments (peptides) identified in the corresponding culture media of *S. thermophilus* LMD9 (wild-type strain producing IL-10 or elafin, respectively). The shaded background shows the regions of IL-10 and elafin proteins corresponding to the peptides identified in the *S. thermophilus* LMD9 culture media. These regions group all the identified peptides. Cysteines (C) are indicated in bold.

FIG. 6: Immunodetection of elafin in culture supernatant of *S. thermophilus* CNRZ1066 (wild type and ΔhtrAΔSTER 1612 double mutant strain).

FIG. 7: Effect of inactivation of surface proteolysis on elafin activity produced by *S. thermophilus* CNRZ1066 (wild-type strain in black and ΔhtrAΔSTER 1612 double mutant in gray).

FIG. 8: Immunodetection of elafin produced by *S. ther-mophilus* CNRZ1066 (wild type and ΔhtrAΔSTER 1612 double mutant strain) and *L. lactis* IL1403 (wild type and ΔhtrA mutant strain).

FIG. 9: Comparison of elafin activities produced by *L. lactis* IL1403ΔhtrA (denoted IL1403D) and *S. thermophilus* CNRZ1066ΔhtrAΔSTER_1612 (denoted CNRZ1066DD).

FIG. 10: Immunodetection of elafin produced by *L. lactis* IL1403 (wild-type and ΔhtrAΔywdF double mutant strain).

FIG. 11: Immunodetection of elafin produced by *L. lactis* MG1363 (wild-type and ΔhtrAΔllmg-2442 double mutant strain).

EXAMPLE 1: CONSTRUCTIONS OF MUTANTS OF THE *STREPTOCOCCUS THERMOPHILUS* LMD9 BACTERIUM STRAIN AND THE *STREPTOCOCCUS THERMOPHILUS* CNRZ1066 BACTERIUM STRAIN

1) Construction of ΔhtrA, ΔprtS and ASTER 1612 Single Mutants of *S. thermophilus* Strain LMD9

General Principle

The single mutants ΔhtrA, ΔprtS and ΔSTER_1612 are constructed from the wild type *S. thermophilus* LMD9 strain by gene replacement. The technique used consists in pro-ducing a PCR fragment combining three amplicons:

an upstream amplicon corresponding to a region located at the beginning of the gene to be replaced, an antibiotic resistance cassette and a downstream amplicon corresponding to a region located at the end of the gene to be replaced.

The three amplicons are produced separately and then combined via a final additional PCR. This association is made possible by adding extensions to the oligonucleotides used to amplify the upstream and downstream regions that allow binding to the antibiotic resistance cassette (PCR overlap). This final PCR fragment is then introduced into the strain by natural competence (WO2010/125091). The homology between the upstream and downstream fragments of the gene and the PCR fragment allows recombination at the site of the gene to be replaced. Colonies with the targeted gene replaced by the resistance gene can be easily isolated on a medium containing the corresponding antibiotic.

Mutant htrA

A kanamycin resistance cassette is used. The upstream and downstream regions of the htrA gene are amplified separately by PCR from *S. thermophilus* LMD9 chromosomal DNA; the kanamycin resistance cassette is amplified from the plasmid pKa (Trieu-Cuot et al., 1983) using the oligonucleotide pairs htrA-upstream-F/htrA-upstream-R, htrA-downstream-F/htrA-downstream-R, and aphA3F/aphA3-R-, the nucleotide sequences of which are shown in Table 1.

TABLE 1

| Oligonucleotides | Sequence | SEQ ID No. |
|---|---|---|
| htrA-upstream-F | GTA ATC ACG GTC ACC AAC C | 16 |
| htrA-upstream-R | GAC ATC TAA TCT TTT CTG AAG TAC ATC CGC AAC AGT AAA CCA CCT AGT AAG CC | 17 |
| htrA-downstream-F | ATA ATC TTA CCT ATC ACC TCA AAT GGT TCG CTG GGT AGT GTT CAG AAA GGT ATG CC | 18 |
| htrA-downstream-R | GGA TTG AGA TTT GAT CGT TG | 19 |
| aphA3-R | GTT GCG GAT GTA CTT CAG | 20 |
| aphA3-F | CCA GCG AAC CAT TTG AG | 21 |

The three fragments are amplified, purified on column with the Clean-Up PCR kit (Promega) and the expected sizes (480 bp, 580 bp and 1350 bp) are verified by agarose gel electrophoresis. An additional PCR combining the three fragments is performed using the three fragments obtained and the htrA-upstream-F and htrA-downstream-R oligonucleotides to obtain a 2410 bp fragment which is purified on column and used to transform the LMD-9 strain according to the following natural transformation protocol A first pre-culture is performed during the day in M17 medium with 1% lactose (M17lac) (Terzagui et al., 1975) from a frozen stock of the strain; from which a second pre-culture in chemically defined medium (CDM) (Letort et al., 2001) is performed overnight. This second pre-culture is used to seed a culture in MCD at an optical density at 600 nm (OD$_{00}$) of 0.05. After 1 h incubation at 42° C., the PCR product combining the three fragments is added to an aliquot of the culture. After incubation at 42° C., the aliquot of culture is spread on M17lac agar plates containing 1 mg/ml kanamycin. The plates are incubated 48 h at 42° C. in anaerobic jar. Several resistant clones are verified by PCR on colony and one clone is then verified by sequencing.

Mutant ΔprtS

An erythromycin resistance cassette is used. The upstream and downstream regions of the ptrS gene were separately amplified by PCR from *S. thermophilus* LMD9 chromosomal DNA; the erythromycin resistance cassette is amplified from plasmid pG+host9 (Biswas et al., 1993) using the oligonucleotide pairs prtS-upstream-F/prtS-upstream-R, prtS-downstream-F/prtS-downstream-R, and erm-F/erm-R, the nucleotide sequences of which are shown in Table 2.

14

TABLE 2

| Oligo-nucleotides | Sequence | SEQ ID No. |
|---|---|---|
| prtS-upstream-F | TGG TAA GCA CGT AGA CC | 22 |
| prtS-upstream-R | CTA CTG ACA GCT TCC AAG GAG CTA AAG AGG TCC CAG GCT TGT CAA TTC ATC TG | 23 |
| prtS-downstream-F | GCA AGT CAG CAC GAA CAC GAA CCG TCT TAT CTC CGA AAG CCA ACT TAG ATG G | 24 |
| prtS-downstream-R | CGT ATG CTT ACC AAC AGA G | 25 |
| erm-F | GGG ACC TCT TTA GCT CCT TGG | 26 |
| erm-R | GGA GAT AAG ACG GTT CGT GTT CG | 27 |

The three fragments were amplified, purified on column and the expected sizes (660 bp, 650 bp and 1060 bp) were verified. An additional PCR combining the 3 fragments is performed using the three fragments obtained and the oligonucleotides prtS-upstream-F and prtS-downstream-R to obtain a 2370 bp fragment which is purified on column and used to transform the LMD-9 strain according to the protocol described above. This culture is then plated on M171ac agar plates containing erythromycin (5 μg/ml) which are incubated 48 h at 42° C. in anaerobic jar. Several resistant clones are verified by colony PCR and one clone is then verified by sequencing.

Mutant ΔSTER_1612.

A spectinomycin resistance cassette is used. The upstream and downstream regions of the STER 1612 gene are amplified separately by PCR from *S. thermophilus* LMD9 chromosomal DNA; the spectinomycin resistance cassette is amplified from plasmid pAT28 (Trieu-Cuot et al., 1990) using the oligonucleotide pairs STER_1612-upstream-F/STER_1612-upstream-R, STER_1612-downstream-F/STER_1612-downstream-R, and spec-F/spec-R, whose nucleotide sequences are shown in Table 3.

TABLE 3

| Oligo-nucleotides | Sequence | SEQ ID No. |
|---|---|---|
| STER_1612-upstream-F | CCC AAC AAC ACC AGG CTC ATT | 28 |
| STER_1612-upstream-R | GAA AAA TTC TAT AGA AAC TTC TCT CAA TTA GGC TAA GGC TGA TCC GGA TGC CAA | 29 |
| STER_1612-downstream-E | TAC AGA TTA ATA ATT ATT CTT TAT TAT ACA GAT CCA GAG TAA TTT CCA GTT GCC | 30 |
| STER_1612-downstream-R | TTC GAG GCC TAC GCA ATG CG | 31 |
| spec-F | GAT CTG TAT AAT AAA GAA TA | 32 |
| spec-R | AGC CTA ATT GAG AGA AGT TTC | 33 |

The three fragments were amplified, purified on column and the expected sizes (596 bp, 957 bp and 566 bp) were verified. An additional PCR combining the 3 fragments is performed using the three fragments obtained and the oligonucleotides STER_1612-upstream-F and STER_1612-downstream-R to obtain a 2050 bp fragment which is purified on column and used to transform the LMD-9 strain according to the protocol described above. This culture is then plated on M17lac agar plates containing spectinomycin (150 μg/ml) which are incubated for 48 h at 42° C. in anaerobic jar. Several resistant clones are verified by colony PCR and one clone is then verified by sequencing.

2) Construction of the ΔhtrA ΔprtS Double Mutant of *S. thermophilus* Strain LMD9

The ΔhtrAΔprtS double mutant is constructed from the ΔprtS single mutant by natural transformation using chromosomal DNA from the ΔhtrA mutant. After breaking the cells with glass beads, the chromosomal DNA of the ΔhtrA mutant is extracted with phenol-chloroform and precipitated with ethanol. The ΔprtS mutant is transformed with purified chromosomal DNA from the ΔhtrA mutant, following the same natural transformation protocol as described above. Transformants are selected by plating on agar medium containing kanamycin (1 mg/ml). Some resistant clones are verified by colony PCR.

3) Construction of the ΔhtrA ΔSTER_1612, ΔprtS ΔSTER_1612 Double Mutants and the ΔhtrAΔprtSΔSTER 1612 Triple Mutant of *S. thermophilus* Strain LMD9

The double mutants ΔhtrA ΔSTER_1612, ΔprtS ΔSTER_1612 and the triple mutant ΔhtrAΔprtSΔSTER 1612 are obtained by natural transformation of the strains LMD9ΔhtrA, LMD9ΔprtS and LMD9ΔhtrAΔprtS with the PCR fragment containing the upstream and downstream regions of the STER_1612 gene fused to the spectinomycin resistance cassette used to construct the single mutant ΔSTER_1612 according to the protocol described above. The mutant selection and control protocol is as described for the LMD9ΔSTER_1612 single mutant.

4) Construction of Mutants of *S. thermophilus* Strain CNRZ1066

The general principle of the construction of the different mutants is identical to the one described above, as well as the protocol used. Only the differences are indicated below.

For single mutants, chromosomal DNA from strain CNRZ1066 is used as a template to amplify the upstream and downstream regions of the gene to be mutated. During natural transformation of strain CNRZ1066, the competence of the strain is stimulated by adding ComS competence peptide (LPYFAGCL) at a concentration of 1 μM for 10 minutes prior to addition of the PCR fragment to the culture.

The CNRZ ΔhtrAΔSTER_1612 double mutant is obtained by natural transformation of the CNRZ1066ΔSTER_1612 strain with chromosomal DNA from the CNRZ ΔhtrA strain. Some mutants were checked by colony PCR.

EXAMPLE 2: DELETION OF THE TWO PROTEASES PRTS AND HTRA DOES NOT ABOLISH SURFACE PROTEOLYSIS IN THE *STREPTOCOCCUS THERMOPHILUS* LMD9 STRAIN OF BACTERIA

Strain LMD9 naturally produces the two surface proteases PrtS and HtrA. To assess their respective roles in the formation of the exopeptidome of strain LMD9, two single ΔprtS and ΔhtrA mutants and one ΔhtrAΔprtS double-mutant were constructed by natural transformation (WO2010/125091), following the protocol described in Example 1.

1) Material and Methods: Determination of the Exopeptidome of Strains

The exopeptidome of the resulting strains is determined under the same experimental conditions as that of the wild-type strain LMD9, as described below.

Culture of the Strain 50 ml of MCD with the concentration of aromatic amino acids (Phenylalanine, Tryptophan and Tyrosine) reduced by a factor of 10 are seeded with 500 μl of standard MCD overnight preculture and incubated at 42° C. until $OD_{600}=1.0$. The cells are then removed by centrifugation (5,000 rpm, 4° C.; 10 minutes), the supernatant is filtered on a 0.22 μm PVDF membrane.

Isolation and Concentration of Peptides.

The filtered culture supernatant is acidified with trifluoroacetic acid (TFA) to a final concentration of 0.1% (470 μl of a 10% TFA solution in 47 ml of culture supernatant), and stored overnight at 4° C.

Peptides present in the acidified supernatant are extracted by solid phase extraction (SPE) on a StrataX cartridge (Phenomenex) containing 200 mg of phase, at a flow rate of about 0.3 ml/min, according to the manufacturer's recommendations. The cartridge is first activated with 3 ml of methanol, then equilibrated with 6 ml of an aqueous solution containing 5% acetonitrile and 0.1% TFA. 1.75 ml of acetonitrile are added to 35 ml of acidified supernatant, so as to have a final concentration of 5% acetonitrile in the supernatant. 35 ml of the prepared supernatant is loaded onto the activated and equilibrated cartridge at a flow rate of 0.3 ml/min. The cartridge is then washed with 5 ml of the aqueous solution containing 5% acetonitrile and 0.1% TFA, and the peptides are eluted with 1.5 ml of an aqueous solution containing 50% acetonitrile and 0.1% TFA. The eluate is dried for 16 to 18 hours by vacuum evaporation (speed vac system) then stored at −20° C.

The dried eluate containing the peptides is taken up with 350 μl of an aqueous solution containing 0.1% TFA (final concentration), which corresponds to a concentration factor of 100. Peptide solubilization is obtained by vortexing and passing 5 minutes in an ultrasonic tank. The concentrated peptide solution is ultrafiltered through a 3 kDa membrane by centrifugation for 1 h at 13000 rpm.

The peptides are then separated by HPLC on a reverse phase column (Kinetex C18 column (Phenomenex), porosity 100 Å, particle size 2.6 μm, size 150×4.6 mm) with a linear gradient (slope 1.6%) of acetonitrile in ammonium formate (20 mM, pH 6.2) at a flow rate of 0.7 ml/min and a temperature of 40° C. The equivalent of 20 ml of culture (i.e. 200 μl of concentrated suspension) is injected on the column. The fractions eluted between 3.2% and 53.3% acetonitrile are collected and dried at speed vac.

Identification of Peptides

Peptide identification is done by mass spectrometry. The dried fractions are taken up in 30 μl of an aqueous solution containing 0.1% TFA and 2% acetonitrile, and a fraction of 4 μl is loaded on a Pepmap C18 column (150×0.075 mm, particle size 2 μm, porosity 100 Å). Peptides are eluted with a gradient of acetonitrile in formic acid (0.1%), and analyzed online by mass spectrometry (LTQ-Orbitrap Discovery, Thermo Fisher). Peptide ionization is done by electrospray (1.3 kV), and the parameters for analysis of the ionized peptides are as follows: measurement of mass/charge ratios (m/z) from 300 to 1600 with a resolution of 15000 on the Orbitrap mass analyzer, and fragmentation of the 6 most abundant parent ions on the LTQ linear trap. The doubly charged peptides are subjected to fragmentation, with a 40 second exclusion window and classical fragmentation parameters (collision energy: 35%).

The identification of peptides and the proteins from which they are derived is done with the X!Tandem search engine (version 2017.2.1.4) and the X!Tandem pipeline software suite (version 3.4.3, www.pappso.fr) using the protein sequence of the *S. thermophilus* LMD9 strain associated with a protein base of contaminants adapted to the analysis activity of the analysis platform (tryptic peptides of a eukaryotic protein sample containing in particular human

EXAMPLE 3: IDENTIFICATION OF A NEW SURFACE PROTEASE IN *STREPTOCOCCUS THERMOPHILUS* LMD9

According to the MEROPS protease and peptidase specific database, the *S. thermophilus* LMD9 genome is reported to contain 45 proteolytic enzymes (merops.sanger-.ac.uk). Genome annotation analysis of this strain (www.ncbi.nlm.nih.gov) suggests the presence of additional proteases, resulting in a total of 52 proteins that may contain a proteolytic domain.

Of these, 11 are predicted to be located on the cell surface based on the LocateP or SecretomeP database. They include PrtS (STER_0846) (STER_RS04165) and HtrA (STER_2002) (STER_RS09790). The hypothesis is that at least one of the remaining 9 proteases is involved in surface proteolysis in *S. thermophilus*.

Of these nine proteases, six are present in *L. lactis* subsp. *lactis* IL1403 and *L. lactis* subsp. *cremoris* MG1363 (Table 4).

TABLE 4

| LMD9 | | | | | | | |
|---|---|---|---|---|---|---|---|
| | Size | IL1403 | | | MG1363 | | |
| Protein | (AAs) | Protein | Size | % Identity | Protein | Size | % Identity |
| STER_0113 | 415 | DacA | 435 | 181/432 (42%) | DacA | 434 | 159/402 (39%) |
| STER_0159 | 265 | DacB | 248 | 132/246 (54%) | DacB | 248 | 122/232 (52%) |
| STER_0260 | 775 | Pbp2A | 743 | 359/628 (57%) | Pbp2A | 743 | 260/472 (55%) |
| STER_1255 | 762 | SrtA | 287 | 134/255 (53%) | SrtA | 250 | 114/214 (53%) |
| STER_1612 | 345 | YwdF | 342 | 169/338 (50%) | Llmg_2442 | 343 | 147/318 (46%) |
| STER_1741 | 207 | SipL | 208 | 109/206 (53%) | SipL | 208 | 99/206 (48%) | keratins, bovine and murine proteins). The X!Tandem pipeline search parameters include the absence of tryptic cleavage for peptide identification, a minimum of one peptide per protein, identified with an E-value less than or equal to 0.01 and a mass tolerance of 10 ppm.

For each bacterial context (wild type, single and double mutants strain), all peptides identified as surface peptides (i.e. peptide resulting from the degradation of a surface protein) are counted. When a peptide is identified several times (identification redundancy), each identification is considered (counting of spectra). Thus a peptide identified once will have a count of 1, a peptide identified three times a count of three. The total number of surface peptides is totaled. As these peptides are derived from surface proteins, they result from the surface proteolytic activity of the strain. The number of peptides counted is therefore an indicator of the intensity of surface proteolysis: the higher the count, the greater the degradation activity, and therefore the surface proteolysis.

2) Results

The results show that both HtrA and PrtS proteases are involved in the formation of the exopeptidome of *S. thermophilus* LMD9. In the double mutant, a reduction of more than half of the number of peptides from surface protein hydrolysis is observed (FIG. 1). A statistical test adapted to small sample sizes (non-parametric Kruskal-Wallis test) indicates that this decrease is statistically significant (P=0.049).

3) Conclusion

The surface proteases HtrA and PrtS alone are not responsible for all the surface proteolytic activity of these strains.

Peptides derived from the degradation of three of these 6 proteases (STER_0260, STER_1612 and STER_1741) were identified in the *S. thermophilus* LMD9 exopeptidome, indicating that these putative proteases were synthesized under these growth conditions. Of these three proteins, STER_0260 is annotated as a D-Ala-D-Ala carboxypeptidase and STER_1741 as a signal peptide peptidase.

The protease STER_1612 (STER_RS07910) (annotated YwdF in IL1403 and llmg_2442 in MG1363, respectively) thus appears to be the candidate protein to participate in surface proteolysis in *L. lactis* and *S. thermophilus*. The presence of a transmembrane fragment in the N-terminal region (www.enzim.hu/hmmtop/) is predicted for the protein in all 3 strains (FIG. 2).

The synthesis of these predictions leads to the hypothesis that the STER_1612 protein would be a cytoplasmic membrane-anchored protease whose active site would be oriented towards the outer side of the membrane.

EXAMPLE 4: DELETION OF THE THREE PROTEASES PRTS, HTRA AND STER_1612 ABOLISHES THE DEGRADATION OF ENDOGENOUS SURFACE PROTEINS

The Inventors hypothesized that the protease STER_1612 in the *S. thermophilus* strain LMD9 and its homologues in *L. lactis* strains, IL1403 and MG1363, were involved in the formation of the *S. thermophilus* and *L. lactis* exopeptidome.

1) Materials and Methods

Validation of this hypothesis was undertaken in the LMD9 strain, by constructing the set of single, double and triple mutants by natural transformation, following the protocol described in Example 1.

In the previously constructed LMD9 wild type, LMD9ΔHtrA, LMD9ΔPrtS and LMD9ΔHtrAΔPrtS strains, the ster 1612 gene was replaced with a spectinomycin resistance cassette.

2) Results

The growth of the strain mutated for the synthesis genes of the three surface proteases is not significantly affected in the culture medium used, a chemically defined medium containing only amino acids as a source of amino nitrogen (see FIG. 3), so that any differences observed between the wild type strain and the mutants cannot be attributed to a difference in growth between the strains.

Inactivation of only one of the three surface proteases reduces the number of peptides from surface protein proteolysis accumulated in the culture medium (exopeptidome surface peptides) by about a factor of 2. When all three proteases are inactivated, this reduction reaches a factor of 25, with only 24 peptides accumulated (average of three independent experiments; see FIG. 4). If we compare the number of peptides accumulated by the htrA_prtS double mutant and the prtS_htrA_ster_1216 triple mutant, the additional inactivation of the STER_1612 protease reduces it by a factor of 9.

3) Conclusion

Surface proteolysis is nearly abolished in the *S. thermophilus* triple mutant, being only 5% of that of the wild type, based on the number of peptides present in the exopeptidome.

EXAMPLE 5: EXTENSION TO OTHER STRAINS OF *STREPTOCOCCUS THERMOPHILUS* NOT POSSESSING THE PRTS PROTEASE

1) Materials and Methods

The role of the two surface proteases HtrA and STER_1612 on the surface proteolysis of *S. thermophilus* strains lacking the PrtS protease was evaluated using strain CNRZ1066 as a representative.

The CNRZ1066ΔhtrAΔprtS double mutant is constructed by natural transformation following the experimental protocol described in Example 1. The exopeptidome of the wild type CNRZ1066 and the resulting mutant are determined under the same experimental conditions as described for the LMD9 strain and its mutants (Example 2).

2) Results

The exopeptidome of wild-type strain CNRZ1066 contains 240 spectra (peptide counts) from surface proteins. The double mutant exopeptidome contains only 15 spectra from surface proteins. Based on the number of spectra identified, the residual surface proteolysis of the CNRZ1066 double mutant can be estimated to be 6% of that of the wild-type strain, a reduction comparable to that obtained with the LMD9 strain.

3) Conclusion

Even though the strain only possesses the two surface proteases HtrA and STER_1612, inactivation of the genes encoding these two proteases is sufficient to reduce the surface proteolysis of the bacteria by more than 90%.

EXAMPLE 6: OBTAINING *STREPTOCOCCUS THERMOPHILUS* STRAINS PRODUCING A HETEROLOGOUS PROTEIN

1) Obtaining *S. thermophilus* Strains Producing IL-10 and Elafin

The *L. lactis* strains LL-pLB350 and LBH832 contain the plasmids pLB350 (Hossain et al., 2012) and pLB386, respectively, which carry the genes encoding IL-10 and elafin, respectively, placed under the control of a bile salt inducible promoter (pGroEL). Plasmids were extracted from these strains and purified using a commercial kit (Midikit, Quiagen).

The two plasmids pLB350 and pLB386 are then introduced into the wild-type *S. thermophilus* strain LMD9 and its triple mutant by natural competence, following the experimental protocol described in Example 1.

Plasmid pLB386 is introduced into wild-type strain CNRZ1066 and its surface protease mutant by natural competence.

Transformants are selected by plating on M17 agar medium containing 5 μg/ml chloramphenicol.

The presence of plasmid pLB350 was then verified by PCR on colonies using the two pairs of oligonucleotides pGroEL-F (ATAATGCCGACTGTACTTT of sequence SEQ ID No. 34)/IL-10-R (GGCCTTGTA-GACACCTTGGTCTT of sequence SEQ ID No. 35) generating a band of 690 base pairs. The plasmid pLB386 was tested with the two pairs of oligonucleotides pGroEL-F and Elafin-R (TCACTGGGGAACGAAACAGGC of sequence SEQ ID No. 36) giving a band of 572 bp and the empty plasmid was tested using the two oligonucleotides Cm-F (GTTCAACAAACGAAAATTGG of sequence SEQ ID No. 37) and Cm-R (TTATAAAAGCCAGTCATTAG of sequence SEQ ID No. 38) giving a band of 807 bp.

EXAMPLE 7: A NON-PROTEOLYTIC BACTERIA STRAIN IMPROVES THE PRODUCTION EFFICIENCY OF HETEROLOGOUS PROTEINS

1) Inactivation of Surface Proteases Reduces the Degradation of Heterologous Proteins

*LMD9 Strain

Materials and Methods

Two heterologous protein models were chosen, interleukin 10 (IL-10) and elafin. Both proteins are candidate proteins in the treatment of chronic inflammatory bowel disease (Benbouziane et al., 2013 and Bermudez-Humaran et al., 2015). The plasmid carrying the gene encoding IL-10 was extracted from the *lactococcus* strain that contained it and introduced into the *S. thermophilus* strain LMD9 and its triple mutant lacking surface proteolytic activity by natural transformation, following the protocol described in Example 6. The same operation was performed for the plasmid encoding elafin. Four strains were obtained, two wild type strains producing IL-10 and elafin and two protease mutants producing the same two heterologous proteins.

To assess the stability of IL-10 and elafin, the two pairs of wild-type and mutant strains carrying plasmid pLB350 and plasmid pLB386, respectively, are grown for 4 h in MCD at 42° C. An equiperal mixture of cholic acid and deoxycholic acid is then added to the culture medium, at a final concentration of 150 μg/ml. The purpose of this addition is to induce the expression of genes controlled by the pGroESL promoter. After 15 minutes of induction at 42° C., the cells are removed by centrifugation and the peptides present in the culture supernatant are identified as shown in Example 2. The only difference is the modification of the interrogation library, to which the sequence of IL-10 or elafin was added, depending on the pair of strains considered.

Results

Several degradation fragments of the heterologous proteins are detected in the culture medium of the wild-type strains, covering in total more than 30% of their respective sequence (see Table 5 and FIG. 5). Under the same experimental conditions, no fragments are detected in the triple mutants. Thus, inactivation of the three surface proteases abolishes the degradation of the two heterologous proteins in *S. thermophilus* LMD9.

TABLE 5

Number of peptides from IL-10 or elafin degradation present in the culture medium of *S. thermophilus* LMD9 and its mutant of the three surface proteases PrtS, HtrA and STER_1612.

| Strain | Wild | Triple mutant protease |
|---|---|---|
| Number of peptides from IL-10 | 9 | 0 |
| Number of peptides from elafin | 43 | 0 |

The results obtained with the two protein models being of the same nature, the rest of the work focused only on one model, elafin.
Strain CNRZ1066
The same experiments were conducted on strain CNRZ1066.

Materials and Methods

The plasmid encoding elafin is extracted from the lactococcal strain containing it, and introduced into the wild-type and mutant strains of CNRZ1066 by natural competence. To evaluate the stability of elafin, their degradation fragments are looked for in the culture medium after 4 h of growth, following the same approach developed for the LMD9 strain.

Results

Thirty-six spectra from elafin are identified in the supernatant of the wild-type strain. The region of elafin covered by the degradation products is the same as in the case of strain LMD9, and represents 40% of the total sequence (see FIG. 5). Under the same experimental conditions, no elafin degradation fragment is detected in the double mutant.

Conclusion

No heterologous protein degradation fragment is found in the supernatant of an *S. thermophilus* strain mutated for its surface proteases, regardless of whether this strain possesses the PrtS protease.
2) Reduced Degradation of Heterologous Proteins Correlates with Increased Production of the Intact Protein
Since the results are comparable whether the *S. thermophilus* strain has two or three surface proteases, further work focuses on only one strain, CNRZ1066. Since no elafin degradation fragment is detected in the double mutant supernatant, it is necessary to ensure that the protein is produced in this strain, and at a higher level than in the wild type strain.

Materials and Methods

This was done by immunodetection of whole elafin in the supernatant (since the protein is secreted into the external environment by the streptococcal strain), using the following experimental protocol.
Culture and induction of elafin production by strains carrying plasmid pLB386 is performed as described in Example 6. After 15 min of induction, the cells are removed by centrifugation, and the supernatant containing elafin is filtered through a 0.22 μm pore size filter (low protein adsorption PVDF membrane). Ten ml of supernatant is concentrated by a factor of 20 by ultrafiltration on 3 kDa cut-off membrane (Amicon ultracell 3 k, MerckMillipore). Five μl of retentate are deposited on polyacrylamide gel (NuPAGE 4-12% Bis-Tris Gel, Invitrogen). After migration for 1 h at 110 mA and 200V, proteins are transferred onto a PVDF transfer membrane (Trans-Bot Turbo Mini transfer pack, Bio-Rad). Elafin, after being labeled with a mouse monoclonal anti-elafin antibody (SantaCruz Biotechnology), is detected by chemiluminescence (ECL Plus Western kit, Pierce).

Results

Several strains are used in these experiments, carried out several times and systematically giving the same results; illustrated for one of them in FIG. 6:
The wild type and mutated *S. thermophilus* CNRZ1066 strains do not produce elafin (wells 3 and 4, labeled pls empty). No bands are observed, indicating that neither strain produces elafin (nor protein cross-reacting with elafin antibody),
The wild type CNRZ166 strain producing elafin (well 5, noted WT pls elafin). Two bands are observed, the upper of which migrates at a very slightly smaller size than the mature form of commercial elafin. The second migrates at a significantly smaller size, and would be a truncated form of the degrading elafin,
Strain CNRZ1066 mutated for its elafin-producing surface proteases (well 6, denoted elafin pls mutant). The lower band corresponding to the truncated form of elafin is no longer detected, only the band corresponding to mature elafin is revealed.

Conclusion

Inactivation of surface proteolysis abolishes elafin degradation in *S. thermophilus*.
3) Inactivation of Surface Proteases Induces an Increase in the Enzymatic Activity Carried by Elafin Materials and Methods The activity of elafin accumulated in the supernatants of wild-type and mutant CNRZ1666 strains is assessed by determining the inhibitory potency of the activity of a control human protease (elastase), following the protocol described below.
*S. thermophilus* strains carrying the pLB386 plasmid are grown in MCD at 37° C. to an $OD_{600}$ of 1.0.
*L. lactis* strains carrying the same plasmid are grown at 30° C. in lactococcal-specific MCD (Otto et al., 1983) to an $OD_{600}$ of 1.0.
At this stage of growth, the cultures are centrifuged, and the cells resuspended in fresh MCD at an $OD_{600}$ of 2.0.
Elafin production is obtained by induction with bile salts (15 ng/ml) and overnight incubation at 37° C. The cells are then centrifuged, and the elafin contained in the supernatant is concentrated by ultrafiltration by a factor of about 300.
Elafin is a protease inhibitor. It is therefore measured according to the following principle. The activity of a human protease (elastase) is measured by fluorescence using a labeled substrate (EnzCheck® Elastae assay kit, Molecular Probes), in the presence and absence of supernatant containing elafin. Inhibition intensity (reflecting elastase concentration) is measured by the difference in fluorescence between the measurement without and with elafin over time following the protocol delivered with the assay kit (Molecular Probes).

Results

Elafin activity produced by the strain lacking proteolytic activity increases approximately twofold compared to that produced by the wild type strain (FIG. 7).

Conclusion

Inactivation of surface proteolysis induces a doubling of the elafin activity produced by the strain.

EXAMPLE 8: PRODUCTION OF ELAFIN BY NON-PROTEOLYTIC BACTERIA STRAINS OF THE INVENTION

Elafin production is evaluated for *L. lactis* strain IL1403ΔHtrA and *S. thermophilus* strain CNRZ1066ΔHtrAΔster_1612.

Materials and Methods

Both strains are grown to an identical population level, and induction of elafin production is performed under the optimal conditions for each strain (see Example 7 point 3)).

Results

The results obtained by immunodetection of elafin produced by each of these strains show for strain CNRZ1066, the presence of a band corresponding to the intact protein detected in the protease mutant and the wild type strain, and a truncated form detected in the wild type strain only. For strain IL1403, truncated forms of elafin are still observed in the single ΔHtrA mutant (FIG. 8).

Thus, the lack of elafin degradation is only seen in *S. thermophilus* ΔHtrAΔSter_1612.

Furthermore, results on the elafin activity produced by each of these strains show that elafin activity is 5-10 times higher in *S. thermophilus* CNRZ1066ΔHtrAΔster_1612 than in *L. lactis* IL1403ΔHtrA (FIG. 9).

EXAMPLE 9: MUTANT CONSTRUCTIONS OF THE *LACTOCOCCUS LACTIS* BACTERIAL STRAIN

The *L. lactis* IL1403 and *L. lactis* MG1363 strains lack a plasmid and therefore do not produce the wall protease PrtP (whose gene is carried by a plasmid, Gasson, 1983). The other two surface proteases produced are therefore HtrA (Poquet et al., 2000) and YwdF in IL1403 (or its homolog llmg-2442 in MG1363). The IL1403ΔhtrAΔywdF double mutant, lacking all three surface protease activities PrtP, HtrA, and YwdF, was constructed from the IL1403ΔhtrA strain (Guillot et al., 2016) by homologous double recombination using the heat-sensitive plasmid pGhost9 following the established protocol (Biswas et al., 1993).

The *L. lactis* MG1363ΔhtrAΔllmg-2442 double mutant, lacking the three surface protease activities PrtP, HtrA and llgm-2442, was constructed in two steps from the wild type *L. lactis* MG1363 strain. The first step consisted in inactivating the htrA gene by double homologous recombination, the second in inactivating the Ilgm-2442 gene in the previously obtained single mutant MG1363ΔhtrA, following a strategy identical to that described above for *L. lactis* IL1403.

EXAMPLE 10: OBTAINING ELAFIN-PRODUCING STRAINS OF *LACTOCOCCUS LACTIS*

Plasmid pLB386 was purified from *L. lactis* strain LBH832 as described in Example 6. It was introduced into *L. lactis* strain IL1403, its *L. lactis* IL1403ΔhtrAΔywdf double mutant, and the *L. lactis* MG1363ΔhtrAΔllmg-2442 double mutant by electroporation. The *L. lactis* LBH832 strain is none other than the wild type *L. lactis* MG1363 strain carrying the plasmid pLB386.

Selection of transformants and the presence of plasmid pLB386 were performed as described in Example 6.

In parallel, control strains carrying a plasmid without elafin, called empty plasmid (pLB44) were constructed.

Plasmid pLB44 was purified from *L. lactis* strain LBH68 as described in Example 6. It was introduced into *L. lactis* strain IL1403, its double mutant *L. lactis* IL1403ΔhtrAΔwdf, and the double mutant *L. lactis* MG1363ΔhtrAΔllmg-2442 by electroporation. The *L. lactis* LBH68 strain is none other than the wild type *L. lactis* MG1363 strain carrying the pLB44 plasmid.

EXAMPLE 11: INACTIVATION OF SURFACE PROTEASES INCREASES THE AMOUNT OF HETEROLOGOUS PROTEIN PRODUCED BY *LACTOCOCCUS LACTIS*

Materials and Methods

Verification that inactivation of *L. lactis* surface proteases results in an increase in the amount of heterologous protein produced was done by immunodetection of whole elafin. The two pairs of wild type and mutant strains (i.e. not synthesizing PrtP, HtrA, or YwdF/llmg-2442) carrying the plasmid pLB386 or pLB44 were grown at 30° C. in chemically defined medium (Otto et al., 1983). Induction of elafin production and its immunodetection were performed as described in Example 7. It should be noted that the same amounts of supernatant are deposited for each strain, so differences in band intensity will reveal differences in protein concentration in the culture supernatant.

Results

Several strains are used in these experiments, performed twice and giving systematically the same results, illustrated respectively for *L. lactis* IL1403 and *L. lactis* MG1363 by FIGS. 10 and 11:

Wild-type and mutated *L. lactis* IL1403 and MG1363 strains not producing elafin (wells 4 and 6, labeled WT pls empty and Mutant pls empty, respectively). No bands are observed, indicating that neither strain produces elafin (or protein that cross-reacts with the elafin antibody), The wild-type strain of *L. lactis* IL1403 producing elafin (FIG. 10, well 3, noted WT pls elafin). Two low intensity bands are observed, the upper of which migrates at a very slightly smaller size than the mature form of commercial elafin. The second migrates at a significantly smaller size (6 kDa), and is thought to be a truncated form of the degrading elafin, The wild-type strain of *L. lactis* MG13633 producing elafin (FIG. 11, well 3, noted WT pls elafin). Two very low intensity bands can be seen, the upper of which migrates at a size very slightly smaller than that of the mature form of commercial elafin. The second migrates at a significantly smaller size (10 kDa), and would be a truncated form of elafin undergoing degradation. The low intensity of the bands reflects a high degradation activity of elafin, The elafin-producing mutant strain of *L. lactis* IL1403 (FIG. 10, well 5, labelled Mutant pls elafin). The lower band corresponding to the truncated form of elafin is almost not detectable anymore, the band corresponding to mature elafin is revealed in a majority, with a much higher intensity than in the wild type strain, reflecting a very low proteolysis of elafin in the double mutant, The elafin-producing *L. lactis* MG1363 mutant strain (FIG. 11, well 5, noted Mutant pls elafin). Three bands are observed, one of which is of very low intensity (6 kDa) corresponding to the truncated form of elafin also seen in the *L. lactis* mutant 1L1403. The upper band (in the form of a doublet) is the same as that found in the wild type strain, but with a much higher intensity, reflecting a much higher concentration of undegraded elafin in the supernatant of the mutated strain.

Conclusion

Inactivation of surface proteolysis greatly reduces the degradation of elafin, resulting in a higher concentration of the intact form of elafin in the supernatant of a *L. lactis* strain not producing surface protease than in that of a wild-type *L. lactis* strain.

REFERENCES

Benbouziane B. et al, J. Biotechnol, 2013, 168: 120-129
Bermudez-Humaran L. G. et al, Curr. Opin. Microbiol, 2013, 16:278-283
Bermudez-Humaran L. G. et al, Microb. Cell Fact. 2015, 14:26
Bermudez-Humaran L. G. and Langella P., Nat. Biotechnol, 2018, 36:816-818
Biswas I. et al, J. Bacteriol., 1993, 175:3628-3635
Botos I. et al, J. Biol. Chem., 2004, 279:8140-8148
Bron P. A. et al, Cur. Opin. Biotechnol, 2019, 56:61-68
Charrette M. F. et al, Proc. Natl. Acad. Sci. 1981; 87:4728-4732
Cossart P. and Joncquières R., Proc. Natl. Acad. Sci. USA, 2000, 97:5013-5015.
Delorme C. et al, Appl. Environ. Microbiol, 2010, 76:451-460
Desvaux M. et al, Front. Microbiol, 2018, 9:100
Fernandez-Espla M. D. et al, Appl. Environ. Microbiol, 2000, 66:4772-4778
Gardan R. et al, J. Bacteriol, 2009, 191:4647-4655
Gasson M., J. Bacteriol, 1983, 154:1-9
Gottesman S. et al, J. Bacteriol, 1978, 133:844-851
Guillot A. et al, J. Proteome Res, 2016, 15:3214-3224
Hafeez et al, Appl. Microbiol. Biotechnol, 2013, 97, 9787-9799
Hafeez et al, J. Agri. Food Chem. 2015, 63, 7522-7531
Hossain M. S. et al, J. Bacteriol, 2012, 194:5886-5896
Letort C. et al, J. Appl. Microbiol, 2001, 91:1023-1029
Motta J. P. et al, Sci. Trans!. Med. 2012; 4:158ra144
Neirynck S. and Steidler L., Biotechnol. Genet. Eng. Rev, 2006, 22:253-266.
Otto R. et al, FEMS Microbiol. Lett. 1983, 16: 69-74.
Poquet I. et al, Mol. Microbiol, 2000, 35:1042-1051
Shamsi T. N et al, Int. J. Biol. Macromol, 2016, 91:1120-1133.
Siezen R. et al, Ant. Leeuwenhoek, 1999, 76:139-155
Soualmia and El Amri, 2018. Expert Opin. Ther. Pat. 28:93-110
Terzagui B. E. et al, Appl. Microbiol, 1975, 29:807-813
Trieu-Cuot P. et al, Gene, 1983, 23:331-341
Trieu-Cuot P. et al, Nucleic Acids Res, 1990, 18: 4296
Wei C. et al, J. Genet. Genomics, 2013, 40:281-289

The invention claimed is:

1. A gram-positive bacterium of the species *Streptococcus thermophilus* or *Lactococcus lactis*, wherein the gram-positive bacterium has been modified to decrease or abolish expression or activity of a surface protease by mutagenesis and to have increased production of a heterologous protein of interest as compared to an otherwise identical gram-positive bacterium that has not been modified to decrease or abolish expression or activity of the surface protease, wherein the surface protease comprises an amino acid sequence having at least 80% sequence identity with the sequence of SEQ ID NO: 1, and wherein SEQ ID NO: 1 is defined as follows:

I-A-G-T-G-T-I-E-X1-D-G-X2-X3-G-X4-I-G-G-X5-X6-X7-K wherein

X1 is histidine (H) or lysine (K);

X2 is serine(S), alanine (A) or threonine (T);

X3 is isoleucine (I), leucine (L) or valine (V);

X4 is aspartic acid (D) or glutamine (Q);

X5 is alanine (A) or valine (V);

X6 is aspartic acid (D) or tyrosine (Y); and

X7 is lysine (K) or leucine (L).

2. The bacterium of to claim 1, wherein the gram-positive bacterium is of the species *Streptococcus thermophilus* and, wherein the surface protease comprises an amino acid sequence having at least 70% sequence identity with the sequence of SEQ ID NO: 2 when the sequences are aligned along their entire length.

3. The bacterium of claim 2, wherein the gram-positive bacterium has been further modified to decrease or abolish expression and/or activity of at least one other surface protease by mutagenesis as compared to an otherwise identical gram-positive bacterium that has not been modified to decrease or abolish expression or activity of the at least one other surface protease, wherein the at least one other surface protease has:

(i) an amino acid sequence having at least 70% sequence identity with the sequence of SEQ ID NO: 8; or (ii) an amino acid sequence having at least 70% sequence identity with the sequence of SEQ ID NO: 9.

4. The bacterium of claim 2, wherein the gram-positive bacterium has been further modified to decrease or abolish expression and/or activity of at least first and second other surface proteases by mutagenesis as compared to an otherwise identical gram-positive bacterium that has not been modified to decrease or abolish expression or activity of the at least first and second other surface proteases, (i) wherein the first other surface protease has an amino acid sequence having at least 70% sequence identity with the sequence of SEQ ID NO: 8; and (ii) wherein the second other surface protease has an amino acid sequence having at least 70% sequence identity with the sequence of SEQ ID NO: 9.

5. The bacterium of claim 1, wherein the gram-positive bacterium is of the species *Lactococcus lactis* and, wherein the surface protease comprises an amino acid sequence having at least 70% sequence identity with the sequence of SEQ ID NO: 3 or with the sequence of SEQ ID NO: 4 when the sequences are aligned over their entire length.

6. The bacterium of claim 5, wherein the gram-positive bacterium has been further modified to decrease or abolish expression and/or activity of at least one other surface protease by mutagenesis as compared to an otherwise identical gram-positive bacterium that has not been modified to decrease or abolish expression or activity of the at least one other surface protease, wherein the at least one other surface protease has:

(i) an amino acid sequence having at least 70% sequence identity with the sequence of SEQ ID NO: 10; or (ii) an amino acid sequence having at least 70% sequence identity with the sequence of SEQ ID NO: 11.

7. The bacterium of claim 5, wherein the gram-positive bacterium has been further modified by mutagenesis to decrease or abolish expression and/or activity of at least first and second other surface proteases as compared to an otherwise identical gram-positive bacterium that has not been modified to decrease or abolish expression or activity of the at least first and second other surface proteases, (i) wherein the first other surface protease has an amino acid sequence having at least 70% sequence identity with the sequence of SEQ ID NO: 10; and (ii) wherein the second other surface protease has an amino acid sequence having at least 70% sequence identity with the sequence of SEQ ID NO: 11.

8. The bacterium of claim 1, wherein the gram-positive bacterium comprises an expression vector containing a DNA fragment encoding the heterologous protein of interest or a DNA fragment encoding the heterologous protein of interest inserted in its chromosome.

9. A method for producing a heterologous protein of interest, the method comprising culturing the gram-positive bacterium of claim 8 to produce the heterologous protein of interest.

* * * * *